US009840716B2

(12) United States Patent
Baek et al.

(10) Patent No.: US 9,840,716 B2
(45) Date of Patent: Dec. 12, 2017

(54) RESVERATROL-ENRICHED RICE AND THE USE THEREOF

(71) Applicant: REPUBLIC OF KOREA (MANAGEMENT: RURAL DEVELOPMENT ADMINISTRATION), Suwon-si, Gyeonggi-do (KR)

(72) Inventors: So Hyeon Baek, Jeonju-si (KR); Woon Chul Shin, Iksan-si (KR); Young Jun Mo, Yongin-si (KR); Bo Kyong Kim, Iksan-si (KR); Seong Tshool Hong, Jeonju-si (KR); Sun Yeou Kim, Incheon (KR); Soon Jong Kweon, Suwon-si (KR)

(73) Assignee: Republic of Korea (Management: Rural Development Administration), Gyeonggi-do (KR)

( * ) Notice: Subject to any disclaimer, the term of this patent is extended or adjusted under 35 U.S.C. 154(b) by 75 days.

(21) Appl. No.: 14/652,745

(22) PCT Filed: Dec. 17, 2013

(86) PCT No.: PCT/KR2013/011715
§ 371 (c)(1),
(2) Date: Jun. 16, 2015

(87) PCT Pub. No.: WO2014/098438
PCT Pub. Date: Jun. 26, 2014

(65) Prior Publication Data
US 2016/0040178 A1 Feb. 11, 2016

(30) Foreign Application Priority Data
Dec. 17, 2012 (KR) .................. 10-2012-0147735

(51) Int. Cl.
*C12N 15/82* (2006.01)
*C12N 9/10* (2006.01)
*A61K 31/05* (2006.01)
*A61K 36/899* (2006.01)
*A23L 7/196* (2016.01)
*A23L 33/105* (2016.01)

(52) U.S. Cl.
CPC .......... *C12N 15/8243* (2013.01); *A23L 7/196* (2016.08); *A23L 33/105* (2016.08); *A61K 31/05* (2013.01); *A61K 36/899* (2013.01); *C12N 9/1029* (2013.01); *C12N 15/8257* (2013.01); *C12Y 203/01095* (2013.01); *A23V 2002/00* (2013.01)

(58) Field of Classification Search
CPC .................................................. C12N 15/8243
See application file for complete search history.

(56) References Cited

U.S. PATENT DOCUMENTS 6,974,895 B1 * 12/2005 Paiva ................. C12N 15/8243
426/615

FOREIGN PATENT DOCUMENTS

| JP | 2008-000129 | 1/2008 |
| JP | 2012-187048 | 10/2012 |
| KR | 10-2006-0058301 A | 5/2006 |
| KR | 10-2008-0012483 A | 2/2008 |
| KR | 10-2009-0019882 A | 2/2009 |
| KR | 10-2011-0112783 A | 10/2011 |
| KR | 10-2011-0136093 A | 12/2011 |
| WO | WO 2010-091488 A | 8/2010 |

OTHER PUBLICATIONS no art cited.*
International Search Report for PCT/KR2013/011715 dated Mar. 24, 2014 (English translation).
Stark-Lorenzen, P. et al., "Transfer of a grapevine stilbene synthase gene to rice (*Oryza sativa* L.)," Plant Cell Reports (1997) 16:668-673.
NCBI, GenBank accession No. L00952.1 (Oct. 13, 2000).

* cited by examiner

*Primary Examiner* — Russell Kallis
(74) *Attorney, Agent, or Firm* — Norton Rose Fulbright US LLP

(57) ABSTRACT

The present invention relates to resveratrol-enriched transgenic rice for biosynthesizing resveratrol at high concentration, in which resveratrol synthase genes are expressibly inserted into the 12$^{th}$ chromosome of natural rice, and seed of rice produced therefrom. Further, the present invention relates to a health functional food composition, an animal feed composition, and a pharmaceutical composition for preventing and improving a metabolic disease, including seed of rice produced from the resveratrol-enriched transgenic rice for biosynthesizing resveratrol, in which resveratrol synthase genes are expressibly inserted into the 12$^{th}$ chromosome of natural rice. The seed of rice produced from resveratrol-enriched transgenic rice into which resveratrol synthase genes are inserted, containing high a concentration of resveratrol of the present invention exhibits remarkably superior effects compared to when the same amount of resveratrol is simply ingested. Further, since rice is produced in the form to be used directly as food without an additional process of separating or extracting resveratrol, it may be widely used as food, feed, and medical supplies for preventing and improving a metabolic disease.

14 Claims, 13 Drawing Sheets

Fig 1b

Insertion Regions and T-DNA sequence

1st T-DNA Insertion Initiation Region (SEQ ID NO: 8) [tgtggtgtaaaca]ATTGACGCTTAGACAACTTAATTA--- 1st T-DNA -- P-Ubi ----
(SEQ ID NO: 9) ---GTCGAATGCTTAGTTAACATTAACATGTGTTG[aa] Start of 2nd T-DNA: deleted border & partial deleted P-Ubi
End of 1st T-DNA: Right border(partial)

GTAAACGGCCAGTGAATTCGAGCTCGGTACCCTTG (SEQ ID NO: 10)
2nd T-DNA -- P-3550 --- ---TATTAAGTTGTCTAAGCGTCAATT [gtttacaccacaa] P-Ubi -  (SEQ ID NO: 11)

2nd T-DNA Insertion Termination Region - partial LB cccttttgctttcggagatatgg[tgtttgcttggtaaggtcagtgatgtgggacaca]ttaatttgtcttcacatgtct (SEQ ID NO: 12)

↑                                                              ↑
330872                                                      330907

O. sativa Chr. 12

RESVERATROL-ENRICHED RICE AND THE USE THEREOF

This application is a national phase application under 35 U.S.C. §371 of International Application No. PCT/KR2013/011715, filed Dec. 17, 2013, which claims the benefit of priority to Korean Patent Application No. 10-2012-0147735, filed Dec. 17, 2012, the entire contents of each of which are hereby incorporated by reference.

BACKGROUND OF THE INVENTION

1. Field of the Invention

The present invention relates to a transgenic rice for biosynthesizing resveratrol at high concentration, in which resveratrol synthase genes are expressibly inserted into the $12^{th}$ chromosome of natural rice, and seed of rice produced therefrom. Further, the present invention relates to a health functional food composition, an animal feed composition, and a pharmaceutical composition for preventing and improving a metabolic disease, including seed of rice produced from resveratrol-enriched rice, in which resveratrol synthase genes are expressibly inserted into the $12^{th}$ chromosome of natural rice.

2. Description of the Related Art

Recently in Korea, due to economical growth and a Westernized diet, an intake of fatty substances from foods has increased, and due to a lack of exercise, etc., metabolic diseases such as obesity, diabetes, hyperlipidemia, hypercholesterolemia, and arteriosclerosis have been increasing.

Obesity generally refers to a condition of excessively high body fat. It is regarded as obesity, when the ratio of body fat to the total weight is 25% or more for men and 30% or more for women. Obesity has been known as a direct or indirect cause of many lifestyle-related diseases such as diabetes, hypertension, hyperlipidemia, etc.

Diabetes is a type of a metabolic disease in which insulin secretion is deficient, dysfunctional, etc., (DeFronzo, 1988). It is characterized by hyperglycemia which relates to a high blood glucose level, and is a disorder causing various symptoms and signs due to hyperglycemia and glucose excretion in urine. Recently, due to an increase in obesity rates, especially in abdominal obesity, the incidence of diabetes has been exponentially increasing.

If such metabolic diseases are not properly treated, various abnormal symptoms are accompanied. Representatively, there are higher risks of renal disorders, neuropathies, strokes due to blood vessel disorders, kidney or heart diseases, diabetic foot ulcers, and cardiovascular diseases. These complications lower the quality of life, and ultimately shorten the lifetime of patients. Current methods of treating the metabolic disease include lifestyle modifications (a dietary therapy and an exercise therapy), a medicinal therapy, etc. However, it is difficult to strictly control or enforce a dietary therapy or an exercise therapy, and there are limitations in therapeutic effects. Therefore, the development of foods for treating a metabolic disease, etc., which may be easily applied in real life is greatly needed.

Meanwhile, resveratrol, a product of resveratrol synthase (RS) gene, is a product of phytoalexin which is one of defensive substances produced in response to environmental stress by external stimuli such as UV, pathogenic bacteria, wounds, etc., (Dercks and Creasy, 1989), and is biosynthesized by catalytic activity of resveratrol synthase (RS) using one molecule coumaroyl-CoA and three molecule malonyl-CoA (Rolfs and Kindl, 1984; Halton and Cornish, 1995).

Although resveratrol is found in more than about 72 types of plants such as grapes, mulberries, peanuts, lilies, etc., it is not biosynthesized at all in most major cereal crops such as rice, corns, wheat, etc., fruits, and vegetables (Aggarwal et al., 2004).

Further, besides the above-described effects of pharmacological actions, resveratrol is also known as a substance activating Sirt-1, a protein associated with life prolongation. Sirt-1 protein is one of proteins associated with life prolongation by prolonging life of cells, following activation by NAD+ in low-calorie conditions. According to Konrad et al. (2003), while Sirt-1 proteins are activated by NAD+ only when calories are limited, when resveratrol is added, Sirt-1 proteins are activated as in low-calorie conditions and increase the life span of yeasts by 70% on average when resveratrol is added in an experiment involving yeasts.

Resveratrol having such physiological activity is synthesized in more than 72 species of plants, and is always synthesized in woody plants such as pines, etc. However, in herb species, it is biosynthesized as a self-defensive substance in response to external stresses such as wounds by phytoalexin activity, damage by ozone, UV, pest infection, etc. Plants with the highest resveratrol biosynthesis are grapes and peanuts (Schroder et al., 1990).

Red wine contains resveratrol, and its consumption is negatively correlated with cardiovascular disease incidences. This is called the French Paradox (Wu et al., 2001) and led to worldwide attention on red wine.

Accordingly, in order to artificially increase the content of resveratrol, research has been conducted to inoculate grapes with strains during cropping, or to treat grapes and peanuts with ultrasonic cleaning or UV irradiation after harvest to increase the content of resveratrol.

Further, research has been conducted to develop crops for biosynthesizing resveratrol by introducing a resveratrol synthase gene isolated from grapes and peanuts via bioengineering methods. It has been reported that 182 μg/g of piceid (resveratrol glycoside) is produced in transformed kiwi plant leaves using a resveratrol synthase gene of grapes (Kobayashi et al., 2000), and 50 ng/g of resveratrol is produced in suspension culture cells of transformed tobacco using resveratrol synthase genes of peanuts (Hain et al., 1990).

P. Stark-Lorenzen et al. has reported that a transgenic rice is resistant to rice blast disease by introducing a stilbene (resveratrol) synthase gene originating from grapes into rice (Plant Cell Reports (1997) 16; 668-673).

Further, the present inventors have disclosed rice produced by introducing conventional resveratrol synthase genes of peanuts in rice (KR Patent Application Publication No. 10-2008-0012483). However, they merely confirmed that resveratrol was contained therein, and failed to provide any evidencing effects of improving metabolic diseases.

The present inventors developed transformed rice, which is a transgenic rice for biosynthesizing resveratrol, at high concentration by inserting resveratrol synthase genes of peanuts into the $12^{th}$ chromosome of natural rice, and confirmed that there exist superior effects of improving a metabolic disease when resveratrol-enriched rice produced from the corresponding rice is ingested, compared to when the same amount of resveratrol is ingested, thereby completing the present invention.

SUMMARY OF THE INVENTION

An objective of the present invention is to provide resveratrol-enriched rice for biosynthesizing resveratrol, in which a resveratrol synthase gene is expressibly inserted into the 12$^{th}$ chromosome of natural rice Another objective of the present invention is to provide seed of rice produced from the rice of the present invention.

Still another objective of the present invention is to provide a health functional food composition for preventing and improving a metabolic disease, including the seed of rice of the present invention.

Still another objective of the present invention is to provide an animal feed composition for preventing and improving a metabolic disease, including the seed of rice of the present invention.

Still another objective of the present invention is to provide a pharmaceutical composition for preventing and improving a metabolic disease, including the seed of rice of the present invention.

The transgenic rice produced from rice into which resveratrol synthase genes are inserted, containing a high concentration of resveratrol of the present invention exhibits remarkably superior effects compared to when the same amount of resveratrol is simply ingested. Further, since rice is produced in the form to be used directly as food without an additional process of separating or extracting resveratrol, it may be widely used as foods, feeds, and medical supplies for functionally preventing and improving metabolic diseases.

BRIEF DESCRIPTIONS OF THE DRAWINGS

FIG. 1a is a schematic diagram illustrating pSB2220 vector, a rice transformation vector capable of transforming unhulled rice with a resveratrol synthase gene.

FIG. 1b is a schematic diagram illustrating analysis results of comparing regions adjacent to a T-DNA insertion region introduced in the transformed rice for biosynthesizing resveratrol of the present invention to sequence data of Nipponbare disclosed in NCBI, which is *japonica* rice having a similarity in sequence with Dongjin rice used in the present invention and having complete sequence analysis. Particularly, nucleotide sequences represented in green are genomic sequences of rice adjacent to the insertion regions of rice, and with respect to the Nipponbare sequence disclosed in NCBI, the first T-DNA insertion initiates at the 330872$^{nd}$ base position of the 12$^{th}$ chromosome of rice (*Oryza sativa*), followed by the second T-DNA insertion in the opposite direction and the termination of insertion at the 330907$^{th}$ base position.

FIG. 2 is a schematic diagram illustrating the effects of rice produced from the transformed rice for biosynthesizing resveratrol of the present invention on blood glucose in animal models induced with a metabolic disease. In the drawing, CTL refers to the control group, DJ to Dongjin rice, res to resveratrol, and GMO to the transformed rice of the present invention.

FIG. 3a-d is a schematic diagram illustrating the effects of rice produced from the transformed rice for biosynthesizing resveratrol of the present invention on blood lipid metabolism in animal models induced with a metabolic disease. In the drawing, CTL refers to the control group, DJ to Dongjin rice, res to resveratrol, and GMO to the transformed rice of the present invention.

FIG. 4a-c is a schematic diagram illustrating the effects of rice produced from the transformed rice for biosynthesizing resveratrol of the present invention on a weight change and the total fat in animal models induced with a metabolic disease. In the drawing, CTL refers to the control group, DJ to Dongjin rice, res to resveratrol, and GMO to the transformed rice of the present invention. Further, in the drawing, CT refers to computational tomography, TF to the total fat, SF to subcutaneous fat, and VF to visceral fat.

FIG. 5 is a schematic diagram illustrating the effects of the transformed rice for biosynthesizing resveratrol of the present invention and the control transformed rice on the level of blood glucose in animal models induced with a metabolic disease. In the drawing, CTL refers to the control group, DJ to Dongjin rice, res to resveratrol, GMO to the control transformed rice, and HFD to high fat feed.

FIG. 6 is a schematic diagram illustrating the effects of the transformed rice for biosynthesizing resveratrol of the present invention and the control transformed rice on blood lipid metabolism, especially on the total cholesterol in blood, in animal models induced with a metabolic disease. In the drawing, CTL refers to the control group, DJ to Dongjin rice, res to resveratrol, GMO to the control transformed rice, and HFD to high fat feed.

FIG. 7 is a schematic diagram illustrating the effects of the transformed rice for biosynthesizing resveratrol of the present invention and the control transformed rice on blood lipid metabolism, especially on the amount of natural fat in blood, in animal models induced with a metabolic disease. In the drawing, CTL refers to the control group, DJ to Dongjin rice, res to resveratrol, GMO to the control transformed rice, and HFD to high fat feed.

FIG. 8 is a schematic diagram illustrating the effects of the transformed rice for biosynthesizing resveratrol of the present invention and the control transformed rice on blood lipid metabolism, especially on the amount of HDL in blood, in animal models induced with a metabolic disease. In the drawing, CTL refers to the control group, DJ to Dongjin rice, res to resveratrol, GMO to the control transformed rice, and HFD to high fat feed.

FIG. 9 is a schematic diagram illustrating the effects of the transformed rice for biosynthesizing resveratrol of the present invention and the control transformed rice on blood lipid metabolism, especially the amount of LDL in blood, in animal models induced with a metabolic disease. In the drawing, CTL refers to the control group, DJ to Dongjin rice, res to resveratrol, GMO to the control transformed rice, and HFD to high fat feed.

DESCRIPTION OF THE PREFERRED EMBODIMENTS

Figure 1A:
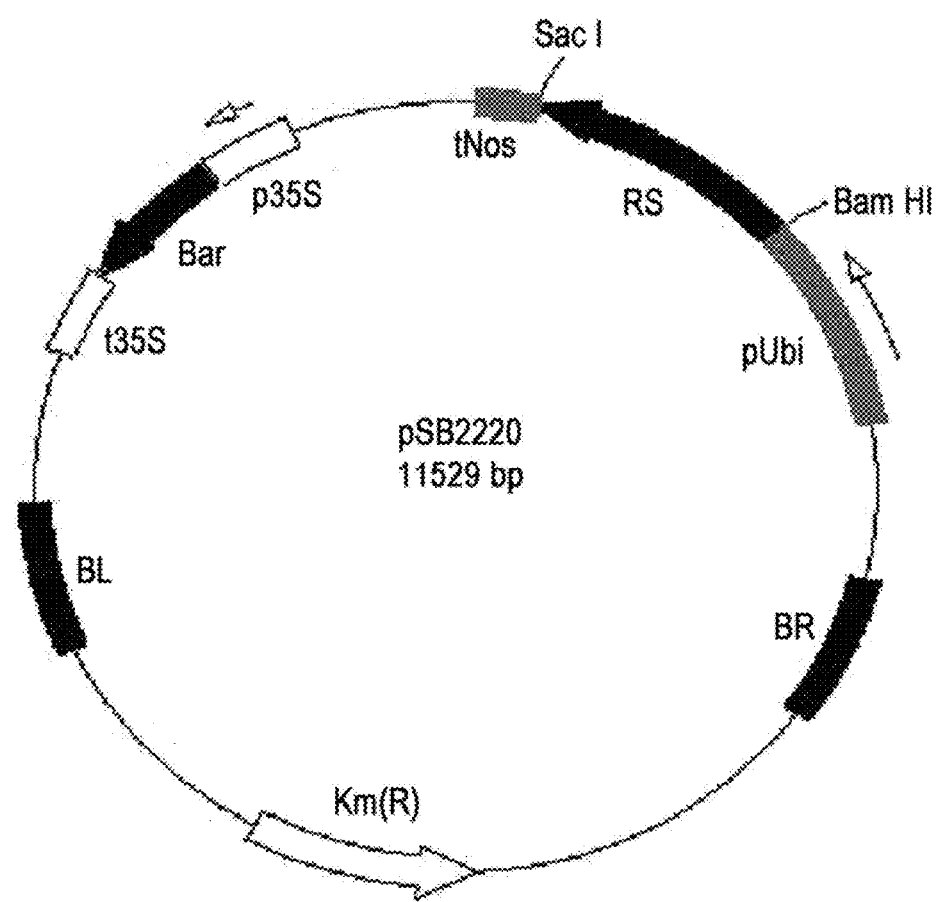

In one aspect of achieving the objectives, the present invention provides rice for biosynthesizing resveratrol, wherein resveratrol synthase genes are expressibly inserted into the 12$^{th}$ chromosome of natural rice.

As used herein, the term "rice" refers to a major food resource of more than half of the world population and to crops harvested as edible crops especially in Asia. It refers to those harvested as crops among plants of the rice genus, and it is known that rice genus includes 20 to 30 wild species, and that among these, *Oryza sativa* and *Oryza glabemima* are only two cultivar species. In the present invention, rice may be natural rice or transgenic rice, and preferably be Dongjin rice, which is a certificated seed developed and distributed in Korea, or transgenic rice thereof.

As used herein, the term "transgenic" or "transformation" refers to any activity which develops or removes a certain character via mutation such as insertion, deletion, or substitution in a DNA nucleotide sequence, and especially in the present invention, it refers to change in genetic properties by external DNA. As used herein, the term "transformed rice" or "transgenic rice" refers to rice in which mutation has occurred in a DNA nucleotide sequence, compared to natural rice produced by transformation, and includes a genetic recombinant produced from induction of insertion or modification of a certain gene, or mutation in activity via genetic recombination technology.

As used herein, the term "resveratrol" refers to a polyphenol-based substance having strong anti-oxidative characteristics, which is produced when a plant faces unfavorable conditions such as fungi or vermin, and is known to be present in abundance in grape peels, grape seeds, peanuts, etc. Much research on effects of resveratrol on humans has been conducted, and effects of anti-cancer, anti-virus, neuroprotection, anti-aging, anti-inflammatory, life prolongation, etc., are known. Resveratrol exists in cis- and trans-forms, and only trans-resveratrol is expected to have medicinal effects.

As used herein, the term "resveratrol synthase gene" refers to a gene (nucleotide sequence) encoding an enzyme which functions to synthesize resveratrol, and may include all enzymes which ultimately function to synthesize resveratrol, irrespective of substrates. In the present invention, the resveratrol synthase gene may originate from *Arachis hypogaea*, and consists of a nucleotide sequence represented by SEQ ID NO: 1.

The resveratrol-enriched transgenic rice for biosynthesizing resveratrol of the present invention may be rice, wherein resveratrol synthase genes are inserted into the 12$^{th}$ chromosome of natural rice. For example, two copies of a resveratrol synthase gene may be consecutively and expressibly inserted in the 12$^{th}$ chromosome. Especially, the two copies of a resveratrol synthase gene may be inserted in an opposing direction from each other.

Further, the rice for biosynthesizing resveratrol of the present invention may be inserted into the region of a nucleotide sequence represented by SEQ ID NO: 7 in the 12$^{th}$ chromosome of natural rice, and especially be inserted after the 572$^{nd}$ base in the nucleotide sequence represented by SEQ ID NO: 7.

Further, the rice for biosynthesizing resveratrol of the present invention may be natural Dongjin rice wherein a resveratrol synthase gene is inserted in a nucleotide sequence represented by SEQ ID NO: 7, especially inserted after the 572$^{nd}$ base in the nucleotide sequence represented by SEQ ID NO: 7, which is present in the 12$^{th}$ chromosome. The region corresponding to SEQ ID NO: 7 of the present invention, in which a resveratrol synthase gene is inserted, may be changed by various natural or artificial mutations in the chromosome of rice. Therefore, the region in which a resveratrol synthase gene is inserted in the present invention may have a homology of 80% or more, preferably 90% or more, and most preferably 95% or more with the nucleotide sequence represented by SEQ ID NO: 7, as long as it facilitates expression of resveratrol synthase gene.

The rice for biosynthesizing resveratrol of the present invention may include not only variable species, cross-breeds, etc., for adding or removing a character for a certain breeding condition and a certain phenotype using the rice of the present invention, but also random mutants modified by various methods for inducing mutation conventionally used in the breeding research field may be included, as long as it maintains the effects of biosynthesizing resveratrol of the present invention.

The methods for inducing mutation of the present invention may include radiation such as electromagnetic waves, particles, X-rays, γ-radiation, alpha rays, beta rays, ultraviolet rays, etc.; chemical mutation induction such as intercalating agents (acridine orange, proflavin, acriflavin, etc.), base analogues (5'-bromouracil, 2'-aminopurine, etc.), DNA modifying agents (Nitrous acid, Hydroxylamine (NH$_2$OH), alkylating agent (MMS, EMS, sodium azide), etc.); etc., but is not limited thereto.

The rice of the present invention may be rice deposited under Accession No. KCTC12529BP.

The rice of the present invention may contain about 2 μg/g to 5.3 μg/g of resveratrol in the case of brown rice and about 1.8 μg/g to 4.1 μg/g of resveratrol in the case of milled rice, when matured.

As used herein, the term "piceid" refers to a glycoside of resveratrol, and is known as a main ingredient of *Polygonum cuspidatum* root, which is used in Chinese herbal remedies.

The rice of the present invention preferably may comprise about 1.0 μg/g to 6.5 μg/g of piceid in the case of milled rice upon maturation.

In one embodiment, the present invention confirms that when a resveratrol synthase gene originating from *Arachis hypogaea* was separated and inserted into rice, the corresponding genetic sequence was the same as SEQ ID NO: 1. It was confirmed that for the transformed rice seed, which is confirmed to biosynthesize resveratrol at high concentration in the present invention, the corresponding resveratrol synthase gene was inserted into the 12$^{th}$ chromosome of rice. Particularly, it was confirmed that two T-DNAs were inserted in opposing directions from each other in the same locations in the 12$^{th}$ chromosome of rice (*Oryza sativa*). Especially, sequences adjacent to regions in which T-DNA was inserted were compared to Nipponbare disclosed in NCBI, which is *Oryza sativa japonica* rice having complete sequence analysis, and it was confirmed that a first T-DNA insertion is initiated at the 330872$^{nd}$ base position, followed by a second T-DNA insertion in the opposite direction. The transformed rice of the present invention with such insertion structures could have remarkably superior resveratrol synthesis ability compared to conventional transformed rice. The transformed rice seed was named resveratrol-enriched rice or resveratrol-enriched transgenic rice, and deposited to the Biological Resource Center of Korea Research Institute of Bioscience and Biotechnology under Accession No. KCTC12529BP on Dec. 5, 2013.

Nevertheless, the base position analyzed in the present invention may be modified at a certain level due to errors, which usually occur during the chromosome analysis which analyzes several hundred thousand to several million bases, and may be analyzed differently depending on the method of analysis. However, this is merely an error in analysis methods, not a practical change in location of mutation, and thus does not affect the essence of the present invention. Although the base position of a resveratrol synthase gene in the present invention may be differently analyzed depending on the advance in analysis methods in the future, or changes at the level of nucleotide sequence analysis, etc., it may be reanalyzed or interpreted based on the seed of the present invention deposited to the Biological Resource Center of Korea Research Institute of Bioscience and Biotechnology under Accession No. KCTC12529BP.

Further, the transgenic rice for biosynthesizing resveratrol produced in the present invention was confirmed to include a resveratrol synthase gene inserted in a region of a nucleotide sequence represented by SEQ ID NO: 7, especially after the $572^{nd}$ base in the nucleotide sequence represented by SEQ ID NO: 7, of the $12^{th}$ chromosome of Dongjin rice. When the location of gene insertion was analyzed via NCBI blast, it was confirmed to be in the $12^{th}$ chromosome of NCBI Accession No. NC_008405, which is the nucleotide sequence analysis of *Oryza sativa japonica* rice which is in the classification of Dongjin rice of the present invention.

Especially, it was confirmed to be inserted particularly at the $330872^{nd}$ base position of NC_008405. However, because the base position may change depending on mutations occurring in the process of growth, mating, etc., it is not considered to go beyond the scope of the present invention, if the insertion position may be considered essentially equivalent.

Figure 13:
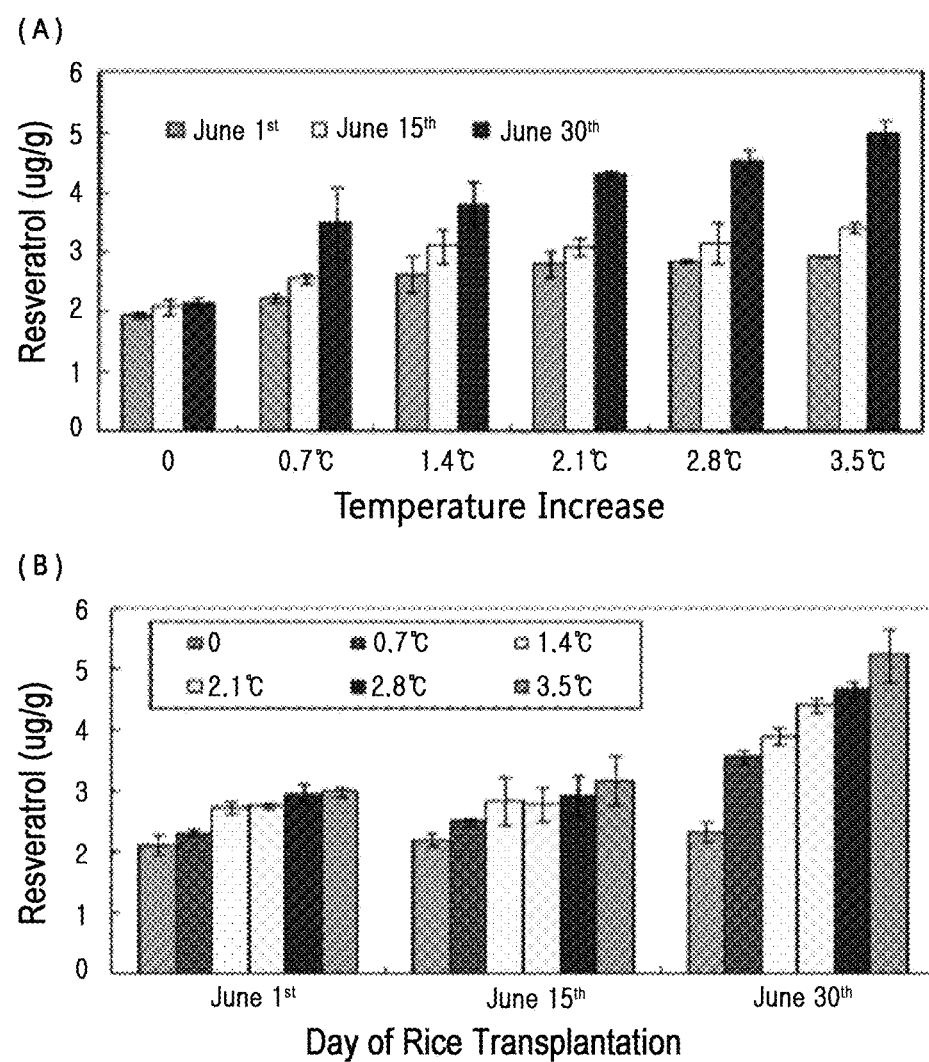
FIG. 13 is a schematic diagram illustrating the content of resveratrol in the seed according to the growing environment, particularly a temperature increase (FIG. 13a) and the day of rice transplantation (FIG. 13b), of the resveratrol synthetic rice of the present invention.

In one embodiment, the present invention confirms that when resveratrol and piceid contained in the brown rice seed of the transgenic rice of the present invention, resveratrol and piceid at high concentration were contained. Particularly, about 1.8 µg/g to 4.1 µg/g of resveratrol, and about 1.0 µg/g to 6.5 µg/g of piceid were contained in milled rice (Table 3), and about 2 µg/g to 5.3 µg/g of resveratrol was contained in brown rice (FIG. 13). Meanwhile, considering that piceid is mainly concentrated in the shells of the rice seed, piceid is expected to be contained at a remarkably higher concentration in brown rice.

In another embodiment, the present invention provides seed of rice produced from the resveratrol-enriched transgenic rice for biosynthesizing resveratrol, wherein two copies of a resveratrol synthase gene are expressibly inserted into the $12^{th}$ chromosome of natural rice. Especially, the present invention provides seed of rice produced from the rice of the present invention.

As used herein, the term "Dongjin rice" refers to a seed produced by three-way cross breeding of Geumnampung and Nakdong rice which is highly resistant to diseases, and Satominori in 1975 with a purpose of developing a new variety of disease resistance, good quality, and high yield. In 1981, it was chosen as a recommended seed in South Korea, named Dongjin rice, and distributed.

As used herein, the term "seed of rice" refers to a seed of rice and includes all conditions regardless of no milling, half milling (brown rice), or full milling (milled rice), as long as it is a seed.

In another embodiment, the present invention provides a health functional food composition for preventing and improving a metabolic disease, including seed of rice produced from resveratrol-enriched transgenic rice for biosynthesizing resveratrol, wherein two copies of a resveratrol synthase gene are expressibly inserted into the $12^{th}$ chromosome of natural rice. Especially, the present invention provides a health functional food composition for preventing and improving a metabolic disease including seed of rice produced from the resveratrol-enriched transgenic rice of the present invention. A metabolic disease to which the food composition of the present invention may be applied may include obesity, diabetes, hyperlipidemia, hypercholesterolemia, artherosclerosis, other cardiovascular diseases, etc. Preferably, a metabolic disease of the present invention may be diabetes or obesity.

As used herein, the term "health functional food" refers to food produced or processed using raw materials or ingredients which are beneficial to the human body according to the law on health functional food No. 6727. The term "functional" refers to food intake for obtaining useful effects on regulating nutrients with respect to the structure and functions of the human body or on health such as physiological applications.

The health functional food composition for preventing and improving a metabolic disease of the present invention may include forms of pills, powders, granules, infusions, tablets, capsules, or liquid. Food to which the composition of the present invention may be added may be, for example, various food products, such as drinks, gum, tea, vitamin complexes, health supplement foods, etc.

As essential components that may be included in the health functional food composition for preventing and improving a metabolic disease of the present invention, a composition for preventing and improving a metabolic disease, including rice produced from rice for biosynthesizing resveratrol, or an active substance thereof, or a pharmaceutically acceptable salt thereof may be included, but is not particularly limited thereto. Like the conventional food, various herbal extracts, food supplementary additives, or natural carbohydrates may be contained as additional components.

Further, as indicated, food supplementary additives may be additionally added, food supplementary additives may include conventional food supplementary additives in the art such as flavors, fragrances, colorings, fillers, stabilizers, etc.

Examples of natural carbohydrates are monosaccharides such as glucose, fructose, etc.; disaccharides such as maltose, sucrose, etc.; and polysaccharides such as conventional sugars such as dextrin, cyclodextrin, etc., and sugar alcohols such as xylitol, sorbitol, and erythritol. Other than those described above, natural flavors such as thaumatin, *stevia* extracts (e.g., rebaudioside A, glycyrrhizin, etc.), and artificial flavors such as saccharine, aspartame, etc., may be used advantageously.

Further to the above, a health functional food composition for preventing or improving a metabolic disease of the present invention may include various nutrients, vitamins, minerals (electrolytes), flavors such as synthetic flavors and natural flavors, coloring agents and fillers (cheese, chocolate, etc.), pectic acids and their salts, alginic acids and their salts, organic acids, protective colloidal thickeners, pH adjusting agents, stabilizers, preservatives, glycerins, alcohols, carbonizing agents used in carbonated drinks, etc. Furthermore, the health functional food composition may include fruit flesh for producing natural fruit juice, fruit juice drinks, and vegetable drinks. These components may be used alone or in combination.

In one exemplary embodiment of the present invention, feeds produced with seed of rice from the resveratrol-enriched transgenic rice including resveratrol at high concentration of the present invention or Dongjin rice seeds were given to animal models (mice) with an induced metabolic disease for 12 weeks via a long-term high fat diet.

Figure 2:
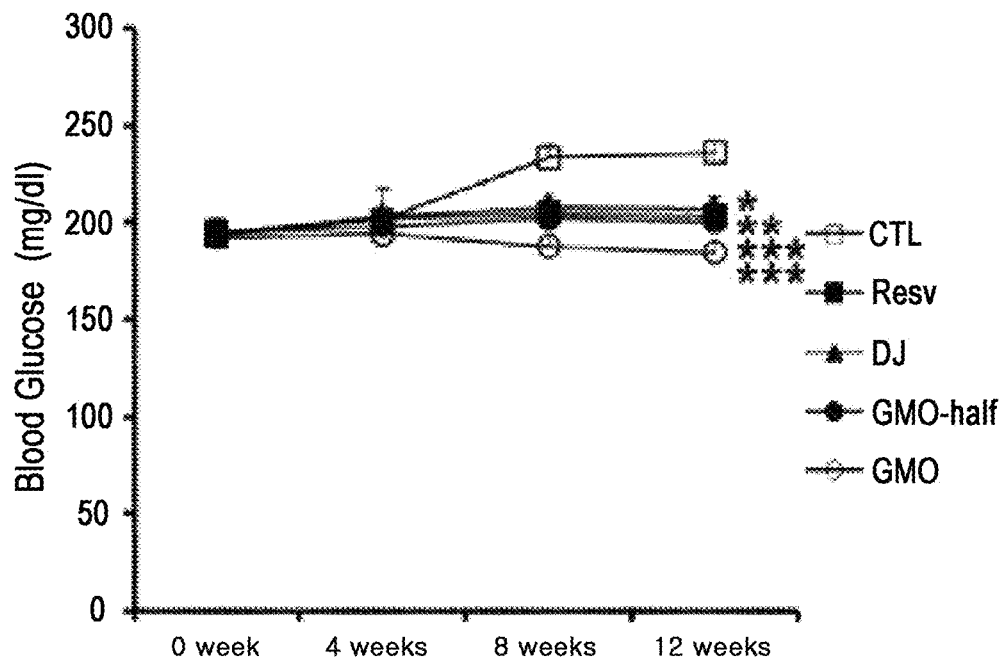
Figure 3A:
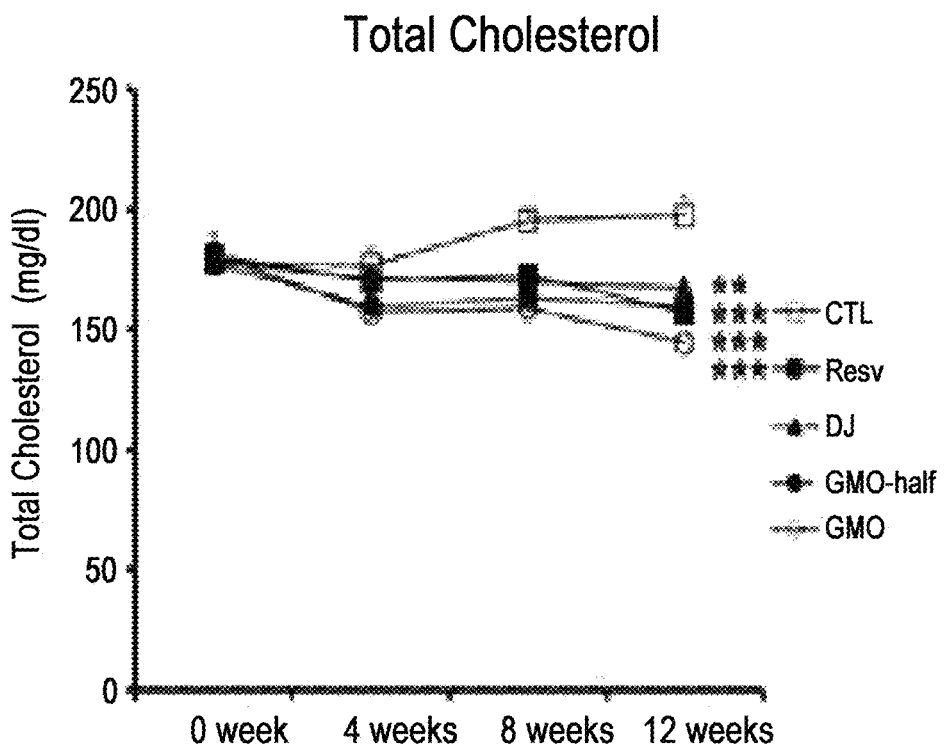
Figure 3B:
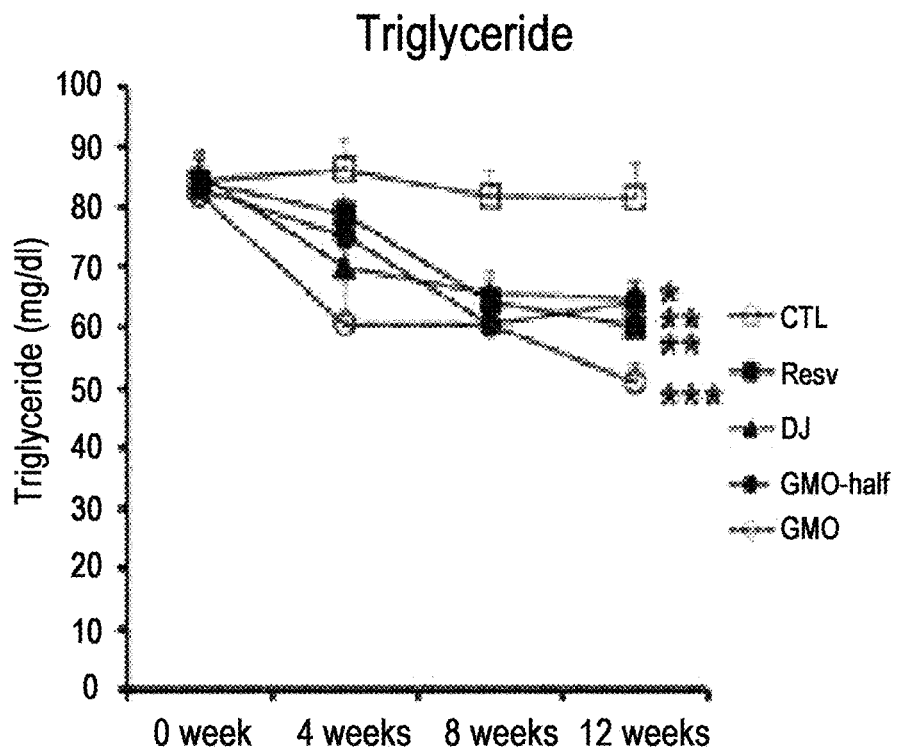
Figure 3C:
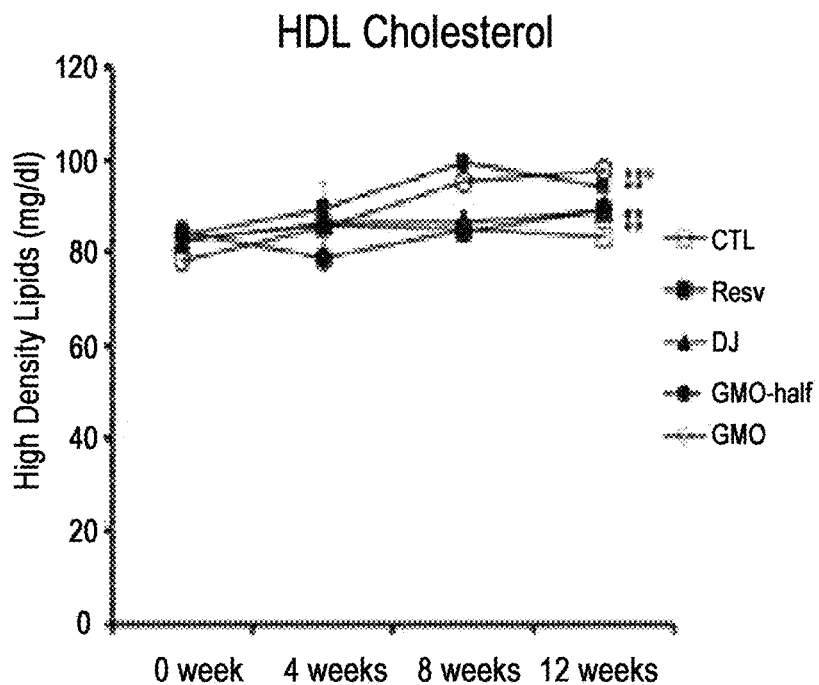
Figure 3D:
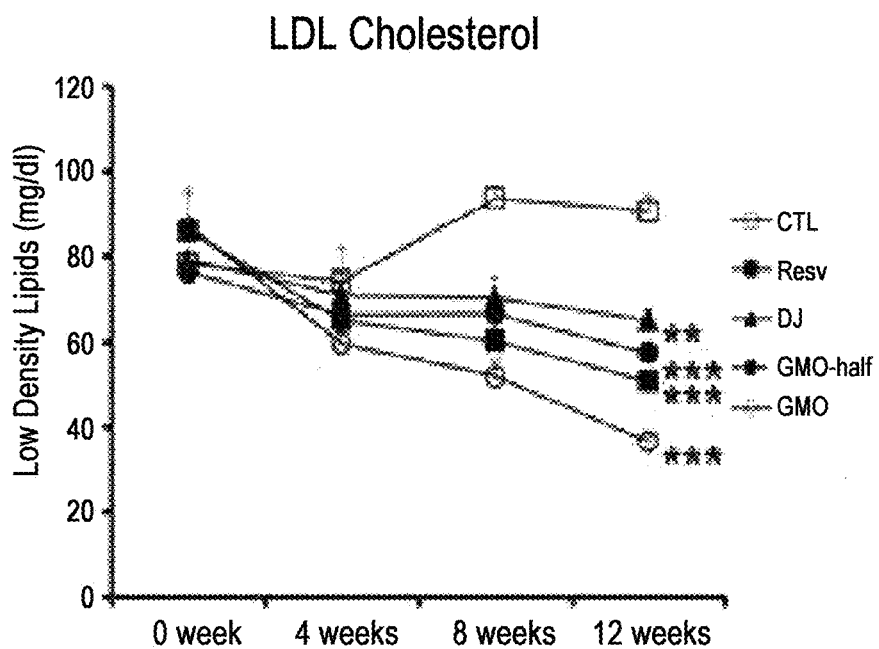

First, after feeding feed in which carbohydrate components are replaced with Dongjin rice and resveratrol-enriched transgenic rice to mice with an induced metabolic disease, blood glucose was measured. Mice which consumed feeds produced from resveratrol-enriched transgenic rice showed a decrease in blood glucose from the $8^{th}$ week, and the blood glucose level dropped by 22.0% in the $12^{th}$ week. On the other hand, the control groups showed equal or increased blood glucose. Further, when fed with general feed including resveratrol (Resv) at an amount equivalent to that of the feed produced from resveratrol-enriched transgenic rice, the mice did not show any noticeable difference, thereby confirming that the effect of resveratrol-enriched transgenic rice on reducing blood glucose is superior to that of simply containing resveratrol (FIG. 2).

Next, after feeding the feed in which carbohydrate components are replaced with Dongjin rice and resveratrol-enriched transgenic rice to mice induced with a metabolic disease, the total cholesterol in blood, the total natural fat in blood, and LDL and HDL cholesterol in blood were measured. Mice which consumed feed produced from resveratrol-enriched transgenic rice showed a reduction of the total cholesterol in blood by 27.0%, the total natural fat in blood by 37.4%, and LDL cholesterol in blood by 59.6%, while showing an increase of HDL cholesterol in blood by 14.8%, which acts to prevent a metabolic disease. On the other hand, other control groups showed no effects or lower effects than the group which consumed the feed produced from resveratrol-enriched transgenic rice. Further, even when compared to the group fed with general feed including resveratrol (Resv) at an amount equivalent to that of the feed produced from resveratrol-enriched transgenic rice, the group which consumed feed produced from resveratrol-enriched transgenic rice exhibited effects of improving blood lipids. This confirmed that the effect of resveratrol-enriched transgenic rice on improving blood lipids is superior to that of simply containing resveratrol (FIG. 3).

Further, after feeding feed in which carbohydrate components are replaced with Dongjin rice and resveratrol-enriched transgenic rice to mice with an induced metabolic disease, weight change and the total fat were measured. Mice which consumed feed produced from the resveratrol-enriched transgenic rice showed a decrease in their weight by 24.7%. Also, when the total fat was measured using in vivo micro CT, the total fat was reduced by 21.55% (control group by 25.43%), visceral fat was reduced by 16.33% (control group by 20.02%), and subcutaneous fat was reduced by 3.1% (control group by 3.83%). Thus, it was confirmed that the total fat was significantly reduced compared to the control group. This confirmed that the effect of resveratrol-enriched transgenic rice on reducing blood glucose exhibits superior effects over simply containing resveratrol.

Meanwhile, in order to compare to the resveratrol-enriched transgenic rice, the present inventors produced the control transgenic rice in which the same resveratrol synthase gene was inserted into the $4^{th}$ chromosome of natural rice, thereby aiming to confirm the excellent effects of the resveratrol-enriched transgenic rice of the present invention. As a result, by confirming that the control transgenic rice, although a resveratrol synthase gene was inserted, did not show a significant difference, compared to natural rice in which the same amount of resveratrol was added, the resveratrol-enriched transgenic rice of the present invention was indirectly confirmed to exhibit superior effects in reducing blood glucose level, blood lipid improvement, weight and body fat reduction, etc.

In another embodiment, the present invention provides an animal feed composition for preventing and improving a metabolic disease, including seed of rice produced from resveratrol-enriched transgenic rice for biosynthesizing resveratrol, wherein two copies of a resveratrol synthase gene are expressively inserted into the $12^{th}$ chromosome of natural rice.

As used herein, the term "animal" refers to an animal which is appropriate for rearing due to a tame behavior in the wild, defined by the Article 2(2)(i) of the Stock Raising Act and each item of the Article 2 of the enforcement regulations thereof. The animal may be cattle, horses, mules, donkeys, goats, gorals, sheep, deer, pigs, rabbits, dogs, cats, poultry, etc.

As used herein, the term "feed" refers to any natural or artificial diet, a meal, or its components for animals to eat, ingest, and digest, or the like. In one embodiment, an animal feed composition including high resveratrol content rice of the present invention may include a concentrated feed, roughages, and/or a special feed.

Concentrated feed may include seed fruits including grains such as wheat, oats, corns, etc.; bran such as rice bran, wheat bran, barley bran, etc., which are byproducts from refining grains; sesame dregs which are byproducts from extracting oil from soybeans, rapeseeds, sesames, coconut palms, etc.; residues such as remaining starch substances which are the main component of starch residues which remain after removing starch from sweet potatoes, potatoes, etc.; fish soluble which is a concentrate of liquid organisms obtained from fish meals, fish wastes, and fish; animal-based feed such as meat meals, blood meals, feather meals, powdered skim milk, dried whey which is obtained from drying whey which is a residue from producing cheese from milk or casein from skim milk, etc.; yeasts, *chlorella*, seaweeds, etc.

Roughages may include fresh grass feed such as wild grass, herbages, soiling, etc.; root vegetables such as turnips for feed, beets for feed, rutabagas which are a type of a turnip, etc; silage, which is a storage feed obtained by filling fresh grass, soiling crops, paper mulberries, etc., in a silo and fermenting with lactic acid; dried grass obtained by cutting and drying wild grass and herbages, straws of crops for breeding stocks; and leaves of beans and plants. Special feed may include mineral feed such as oyster shells, halite, etc.; urea feed such as urea or its derivatives, diureide isobutene, etc.; and feed additives which are added in a small amount into a mixed feed in order to supplement ingredients which may be lacked when only mixing natural feed ingredients or to increase the shelf life of feed.

In another embodiment, the present invention provides a pharmaceutical composition for preventing or improving a metabolic disease, including seed of rice produced from the resveratrol-enriched transgenic rice for biosynthesizing resveratrol, wherein two copies of a resveratrol synthase gene are expressively inserted into the $12^{th}$ chromosome of natural rice. Especially, the present invention provides a pharmaceutical composition for preventing or improving a metabolic disease, including seed of rice produced from the resveratrol-enriched transgenic rice of the present invention.

Seed of resveratrol-enriched rice, which is included in the pharmaceutical composition of the present invention may include not only seed of rice from rice, which was not processed, but also all forms produced from the seed of rice, such as ones processed to activate active substances of seed of rice, rice extracts, rice fractions, etc.

The pharmaceutical composition of the present invention may further include a pharmaceutically acceptable carrier.

The pharmaceutical composition of the present invention may be produced in a pharmaceutical formulation by a method well known in the art in order to provide rapid, sustained, or delayed release of an active substance after administration to a mammal. Regarding the production of a formulation, it is preferred to mix or dilute an active substance with a carrier, or to enclose it into a carrier in a form of a container.

Therefore, the pharmaceutical composition of the present invention may be prepared as a formation by a conventional method in the form of powders, granules, tablets, capsules, suspensions, emulsions, syrups, oral dosage forms such as aerosols, external preparations, suppositories and sterile injections, and may further include carriers, excipients, and diluents, which are conventionally used in preparing compositions.

For example, a carrier that may be included in a composition of the present invention may be lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate and mineral oil, etc., but is not limited thereto. When the preparation is formulated, conventionally used fillers, extenders, binders, wetting agents, disintegrating agents, diluents such as surfactants, etc. or excipients, may be used.

The solid preparation for oral administration may include tablets, pills, powders, granules, capsules, etc., and may be produced by mixing at least one of excipients such as starch, calcium carbonate, sucrose or lactose, gelatin, etc, to the compound. Further, other than simple excipients, lubricants such as magnesium stearate, and talc may also be used.

Liquid formulations for oral administration may be a suspension, solution, emulsion, syrup, etc., and may include not only generally used simple diluents such as water and liquid paraffin, but also various other excipients such as wetting agents, sweeteners, flavoring agents, preservatives, etc.

Formulations for parenteral administration may include sterilized aqueous solutions, non-aqueous solvents, suspensions, emulsions, lyophilized preparations, and suppositories. As a non-aqueous solvent or suspending agent, propylene glycol, polyethylene glycol, vegetable oil such as olive oil, and injectable esters such as ethyl oleate may be used.

As the base of suppositories, witepsol, macrogol, tween 61, cacao butter, laurin, glycerogelatin, etc., may be used.

Hereinafter, the present invention will be described more in detail with reference to Examples, but Examples are for illustrative purposes only, and thus the scope of the present invention is not intended to be limited by the Examples.

EXAMPLE 1

Isolating a Resveratrol Synthase Gene and Sequencing

In order to develop rice for biosynthesizing resveratrol at high concentration using the resveratrol synthase gene of the present invention, the resveratrol synthase gene of *Arachis hypogaea*, which biosynthesizes resveratrol at high concentration, was isolated.

First, pods of *Arachis hypogaea* which was cultivated by the Rural Development Administration of Korea were harvested, finely ground using liquid nitrogen, and the total RNA was separated using TRI agent (MRC, USA). The total RNA was obtained using NucleoTrap mRNA Midi Purification kit (Clontech, USA).

Next, an RT-PCR was performed with a forward/reverse primer using One step RNA PCR kit (Takara, Japan). The RT-PCR was performed by following 1 cycle of reverse transcription at 50° C. for 30 minutes; 1 cycle of denaturing at 94° C. for 2 minutes; and 35 cycles of denaturing 94° C. for 30 seconds, annealing at 57° C. for a minute, and extension at 68° C. for 1 minute. Forward and reverse primers used herein are as follows:

```
Forward primer
                                        (SEQ ID NO: 2)
5'-ATGGTGTCTGTGAGTGGAATTC-3'

Reverse primer
                                        (SEQ ID NO: 3)
5'-CGTTATATGGCCACACTGC-3'
```

The resveratrol synthase cDNA, amplified from the mRNA of *Arachis hypogaea*, was cloned into a gene carrier, pGEM-T Easy vector (Promega, USA), transformed into *E. coli* JM109, and used for sequence analysis. Sequence analysis was performed using a DNA sequencer 4200 of LI-COR (USA) along with T7 and SP6 primers present in the vector (SEQ ID NO: 1).

EXAMPLE 2

Construction of a Vector for Transformation

In order to introduce the resveratrol synthase gene obtained from Example 1 into rice, a vector for transformation was constructed.

Particularly, in order to construct a vector for transformation of rice, ubiquitin promoter was introduced for inducing plant body constitutive expression, and a herbicide-resistant gene, Bar, was introduced as a selection marker, while using pCAMBIA 3300 vector as a backbone. The resultant was named pSB22 vector.

The resveratrol synthase gene of Example 1 was amplified using a forward primer with a sequence targeted by BamH1 restriction enzyme (5'-CGGATCCATGGTGTCTGT-GAGTG-3', SEQ ID NO: 4) and a reverse primer with a sequence targeted by Sac1 restriction enzyme (5'-CGAGCTCCGTTATATGGCCACA-3', SEQ ID NO: 5) via PCR reactions.

PCR reactions were performed following the initial denaturing at 94° C. for 2 minutes; 35 cycles of denaturing at 94° C. for 20 seconds, annealing at 64° C. for 20 seconds, and extension at 72° C. for 50 seconds; and final extension at 72° C. for 7 minutes.

PCR products obtained from the PCR reactions were treated with restriction enzymes, BamH1 and Sac1, and were introduced in pSB22 rice transformation vector. The produced vector from introduction was named pSB2220, and its structure is illustrated in FIG. 1.

EXAMPLE 3

Producing Resveratrol Synthase Gene-Transformed Rice

In order to introduce the pSB2220 vector for transformation of rice produced in Example 2 into rice, the vector was introduced into *A. tumefaciens* (LBA 4404) using a freezing-thawing method (An, 1987; An et al., 1988).

pSB2220-introduced *Agrobacterium* was cultured in a liquid medium of AB ($K_2HPO_4$ 6 g, $NaH_2PO_4$ 2 g, $NH_4Cl$ 2 g, KCl 0.3 g, $MgSO_4.7H_2O$ 0.6 g, $CaCl_2.2H_2O$ 0.025 g, FeSO$_4$.7H$_2$O 0.05 g, Glucose 10 g, DW 10 mL) at 28° C. for 3 days, proliferated, and used in callus infection after concentrating by 10 fold.

Matured brown rice of rice seeds was sterilized with 70% ethanol for 1 minute and with 2% NaClO for an hour. After sterilization, the seeds were washed with sterilized water at least 5 times and cultured in a medium of 2N6 (N6 salt 3.95 g/L, sucrose 30 g/L, casamino acid 1 g/L, 2,4-D 2 mg/L, phytagel 2 g/L, pH 5.6-5.7) at 25° C. under dark conditions for about 3 weeks, thereby inducing callus.

Among the induced rice calluses, one with a diameter of about 3 mm to 4 mm was again put into the 2N6 medium and cultured at 25° C. under dark condition for 4 days. After the cultured callus was mixed with the AB medium in which *Agrobacterium* was cultured, and infected for 20 minutes, it was put into a medium of 2N6 AS100 (2N6, 100 μM acetocyringone) and cultured at 20° C. under dark conditions for 3 days. After the mixed culture, callus was washed with sterilized water, to which 250 mg/L cefotaxime was added, at least 5 times, thereby removing smeared *Agrobacterium* which was not introduced therein.

*Agrobacterium*-infected callus was put into a medium of 2N6-PT5 (N6 salt 3.95 g/L, sucrose 30 g/L, casamino acid 1 g/L, 2,4-D 2 mg/L, phosphinothricin 5 mg/L, cefotaxime 250 mg/L, phytagel 2 g/L, pH 5.6-5.7) and cultured at 25° C. under dark conditions for 4 weeks, followed by selecting callus which showed resistance to phosphinothricin (PPT) selection marker, thus growing actively.

Callus selected from the 2N6-PT5 medium was put into a medium of N6-BA (N6 salt 3.95 g/L, sucrose 20 g/L, sorbitol 30 g/L, casamino acid 2 g/L, 2,4-D 1 mg/L, BAP 0.5 mg/L PPT 6 mg/L, cefotaxime 250 mg/L, phytagel 2 g/L, pH 5.6-5.7) and cultured at 25° C. under dark conditions for 2 weeks, followed by selecting the actively growing callus.

Callus selected from the N6-BA medium was put into a medium of MSR (MS salt 3.95 g/L, sucrose 40 g/L, sorbitol 20 g/L, myo-inositol 100 mg/L, NAA 0.1 mg/L, kinetin 2 mg/L PPT 6 mg/L, cefotaxime 250 mg/L, phytagel 5 g/L, pH 5.6-5.7) and cultured at 25° C. under 16 hours of light conditions for at least one month, followed by differentiation to a plant body.

When redifferentiated rice had a size of about 4 cm to 5 cm in a Petri dish, it was moved into a bottle medium and grown up to 2 to 3 leaf stages, at illumination of about 20,000 lux and 25° C. under 16 hours of light conditions. Next, a young seedling was transplanted in the soil in a GMO greenhouse, and seeds were harvested. Assuming that the present redifferentiated plant body was a T0 generation and that the seeds harvested from the plant body was a T1 generation, progression was made until a T5 generation.

EXAMPLE 4

Verifying Whether a Resveratrol Synthase Gene is Introduced in Transformed Rice 4-1. Simple Verification of Introduction Whether a resveratrol synthase gene was introduced into transformed rice produced in Example 3 was verified via PCR.

Particularly, genomic DNA was isolated from the transformed rice produced in Example 3, and PCR was performed thereafter. The forward and reverse primers used for producing the pSB2220 vector (forward; 5'-CGGATC-CATGGTGTCTGTGAGTG-3', SEQ ID NO: 4, reverse; 5'-CGAGCTCCGTTATATGGCCACA-3', SEQ ID NO: 5) were used in PCR reactions.

PCR was performed following the initial denaturing at 94° C. for 2 minutes; 35 cycles of denaturing 94° C. for 20 seconds, annealing at 64° C. for 20 seconds, and extension at 72° C. for 50 seconds; and final extension at 72° C. for 7 minutes.

The PCR reaction revealed a band of 1.1 kb, which corresponds to a resveratrol synthase gene, thereby confirming that a resveratrol synthase gene was stably inserted into the genome of the transformed rice.

4-2. Analysis of the Insertion Region of the Inserted Gene

In order to verify the location of the resveratrol synthase gene in the genome of transformed rice for biosynthesizing resveratrol of the present invention produced in Example 3, an adaptor was attached after treating restriction enzymes, and PCR was performed thereafter. The PCR product was analyzed via sequencing and confirmed.

Particularly, the genomic DNA was isolated from the transformed rice produced in Example 3 and treated with restriction enzymes. After reacting with HaeIII restriction enzyme at 37° C. for 4 hours, an adaptor (tccctttagtgaggg-taaattg) was attached, and PCR reactions were performed thereafter.

PCR was performed following the initial denaturing at 94° C. for 2 minutes; 35 cycles of denaturing 94° C. for 20 seconds, annealing at 64° C. for 20 seconds, and extension at 72° C. for 50 seconds; and final extension at 72° C. for 7 minutes. Sequencing was performed using a DNA sequencer 4200 of LI-COR (USA) along with T7 and SP6 primers, which are present in rice.

As such, the line of rice, which was confirmed to have the resveratrol synthase gene inserted into the 12$^{th}$ chromosome of rice, was chosen as the transformed (resveratrol-enriched transgenic) rice of the present invention.

4-3. Analysis of the Structure of the Inserted Gene and Sequencing of Adjacent Nucleotide Sequences In order to verify the insertion region of the inserted gene into the genomic DNA and the nucleotide sequences adjacent to the insertion region regarding the transformed rice for biosynthesizing resveratrol of the present invention produced in Example 3, a flanking DNA sequence was analyzed. The fact that two T-DNAs were inserted in the transformed rice of the present invention was analyzed. Also, adjacent nucleotide sequences and the structure of the inserted T-DNA were analyzed. In conclusion, it was confirmed that two T-DNAs were two inserted in opposing directions from each other at the same locations in the 12$^{th}$ chromosome of the rice.

The results of comparing the regions adjacent to T-DNA insertion regions introduced in the transformed rice for biosynthesizing resveratrol of the present invention to sequence data of Nipponbare disclosed in NCBI, which is *japonica* rice having similarities in sequence with Dongjin rice used in the present invention and having complete sequence analysis showed that the first T-DNA was inserted at the 330872$^{nd}$ base position in the 12$^{th}$ chromosome of the Nipponbare sequence disclosed in NCBI (NCBI Accession No. NC_008405), followed by the second T-DNA insertion in reverse. Particularly, it was confirmed that the 330871$^{st}$ base of the 12$^{th}$ chromosome and the insertion initiation region (left border) of the first T-DNA are connected, and the insertion initiation region (left border) of the second T-DNA is connected to the 330908$^{th}$ base of the same chromosome. In conclusion, it was confirmed that two T-DNAs were inserted as a reversely connected single structure in the 12$^{th}$ chromosome of the transformed rice of the present invention (FIG. 1*b*).

The analyzed adjacent nucleotide sequences are found to be a nucleotide sequence represented by SEQ ID NO: 7. Particularly, the resveratrol synthase gene of the present invention was confirmed to be inserted after the $572^{nd}$ base of SEQ ID NO: 7. Thus, it was analyzed that two T-DNAs are consecutively inserted being connected to the $572^{nd}$ base and the $609^{th}$ base of SEQ ID NO: 7.

As such, the transformed rice seed was named resveratrol-enriched rice and was deposited to the Biological Resource Center of Korea Research Institute of Bioscience and Biotechnology under Accession No. KCTC12529BP on Dec. 5, 2013.

EXAMPLE 5

Analysis of Resveratrol Biosynthesis of Transformed Rice

Whether resveratrol is actually synthesized in the transformed rice produced in Example 3 was verified via HPLC analysis.

Particularly, brown rice seeds of the transformed rice of a T5 generation were ground, and 600 mg of powder was put into a 2 mL tube, followed by addition of 600 µL of 30% methanol. The mixture was stirred at 45° C. at a rate of 150 RPM for 50 minutes, thereby extracting resveratrol. After centrifugation of the extraction tube at 4° C. and 10,000 g for 5 minutes, the supernatant was filtered through a 0.2 µm membrane filter, and used for HPLC analysis. Alliance (Waters 2695, Ireland) of Waters and XTerra RP18, 5 µm 4.6 mm×250 mm column (Waters, Ireland) were used for HPLC analysis, and water and acetonitrile were used as solvents for gradient conditions.

Gradient conditions of the water and acetonitrile at a ratio of 90:10 (v/v) from 0 minutes to 5 minutes, and the water and acetonitrile at a ratio of 70:30 (v/v) from 5 minutes to 65 minutes were created and analyzed. The analysis was performed by injecting 10 µL of extracts and measuring at a flow rate of 1.0 mL/min and the wavelength of UV 308 nm. The peak of resveratrol and a complex of resveratrol and a glycoside, piceid (resveratrol-3-O-Dglucoside) were estimated with reference to the UV spectrum and retention time of the standard substance.

The analysis results confirmed that the transformed rice of the present invention produced in Example 3 included resveratrol and piceid at high concentration.

EXAMPLE 6

Growth of Resveratrol Synthetic Rice and Differences in Resveratrol Contents Depending on the Harvest Conditions

EXAMPLE 6-1

Figure 11:
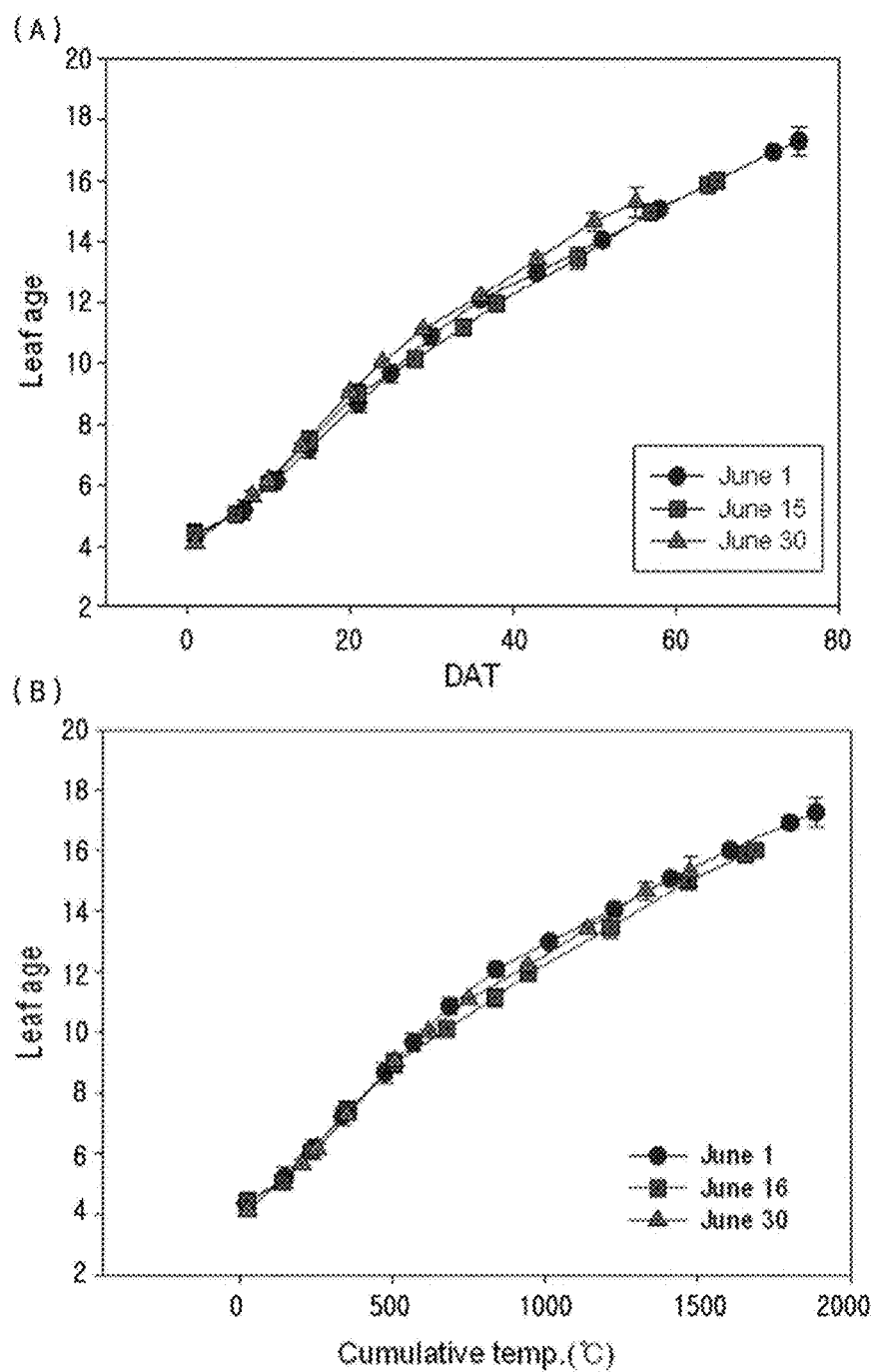
FIG. 11 is a schematic diagram illustrating the heading stage (FIG. 11a) and cumulative temperature (FIG. 11b) according to the day of rice transplantation of the transformed rice for biosynthesizing resveratrol of the present invention.

Characteristics of Growing Rice Under Field Culture Conditions Depending on Rice Transplantation Time The resveratrol synthetic rice of the present invention was transplanted under field culture conditions on June $1^{st}$, $15^{th}$, and $30^{th}$, and the results showed that growth termination of main culm leaves took place 75.1 days, 65.1 days, and 55.1 days after each rice transplantation for June $1^{st}$, 15, and 30, respectively, and the accumulated temperature at each of the times was 1886° C., 1688° C., and 1474° C., respectively. Here, the numbers of developed leaves were 13.0, 11.6, and 11.2, respectively, and rice transplantation on June $1^{st}$ showed a trend of the heading stage being delayed by 4 days to 5 days, compared to a typical mid-late maturing breed (FIG. 11).

As a result, the heading stage of rice transplanted on June $1^{st}$, $15^{th}$, and $30^{th}$ started on August $22^{nd}$, August $27^{th}$, and August $31^{st}$. Therefore, a heading characteristic of a high possibility of incomplete ripening in the case of delayed rice transplantation was observed.

EXAMPLE 6-2

Characteristics of Growing Rice Under High Temperature Culture Conditions (Greenhouse) Depending on Rice Transplantation Time In high temperature conditions, the heading stage of the resveratrol synthetic rice of the present invention was sooner as temperature increased, compared to rice transplantation on June $1^{st}$ under field culture conditions (heading on August $22^{nd}$). As a result, in the conditions of a temperature increase of 3.5° C., the heading stage was advanced by 5 days.

TABLE 1

Changes in heading stage in high temperature culture conditions

| Day of rice transplantation (Month.Day) | Heat treatment | | | | | |
|---|---|---|---|---|---|---|
| | Field culture | +0.7 | +1.4 | +2.1 | +2.8 | +3.5 |
| 6.1 | 8.22 | 8.21 | 8.20 | 8.19 | 8.18 | 8.17 |
| 6.15 | 8.27 | 8.27 | 8.27 | 8.26 | 8.26 | 8.25 |
| 6.30 | 8.31 | 8.31 | 8.31 | 8.31 | 8.30 | 8.30 |

As shown in Table 1, the heading period of rice transplanted on June $15^{th}$ was 2 days sooner than that of under field culture conditions, which was August 27, and the heading period of rice transplanted on June $30^{th}$ was 1 day sooner than that under field culture conditions, which was August $31^{st}$. Thus, the effect of a temperature increase on shortening growth of rice decreased as the day of rice transplantation was delayed, compared to rice transplantation on June $1^{st}$.

EXAMPLE 6-3

Changes in the Amount of Rice Depending on the Day of Rice Transplantation and High Temperature Conditions The changes in the amount of rice depending on the day of rice transplantation and high temperature conditions of the resveratrol synthetic rice of the present invention were measured.

TABLE 2

Changes in the amount of rice depending on the day of rice transplantation and high temperature conditions

| Day of rice transplantation | Temperature | Panicles (#) | Number of grains per panicle (#/panicle) | Ripening ratio (%) | Grain weight of brown rice (g) | Amount of rice (kg/10a) |
|---|---|---|---|---|---|---|
| 6.1 | Field culture | 9.8 | 113.0 | 88.7 | 23.3 | 520 |

TABLE 2-continued

Changes in the amount of rice depending on the day of rice transplantation and high temperature conditions

| Day of rice trans- plan- tation | Temper- ature | Panicles (#) | Number of grains per panicle (#/panicle) | Ripen- ing ratio (%) | Grain weight of brown rice (g) | Amount of rice (kg/10a) |
|---|---|---|---|---|---|---|
| 6.1 | +0.7 | 9.0 | 109.3 | 83.1 | 23.2 | 429 |
| 6.1 | +1.4 | 10.3 | 98.1 | 82.9 | 23.2 | 373 |
| 6.1 | +2.1 | 9.7 | 102.2 | 80.6 | 23.2 | 299 |
| 6.1 | +2.8 | 10.6 | 97.1 | 74.7 | 22.6 | 291 |
| 6.1 | +3.5 | 11.6 | 89.9 | 71.9 | 22.3 | 217 |
| 6.15 | Field culture | 13.2 | 109.9 | 80.0 | 20.5 | 467 |
| 6.15 | +0.7 | 11.7 | 89.0 | 91.2 | 24.7 | 460 |
| 6.15 | +1.4 | 11.0 | 92.5 | 93.6 | 24.4 | 511 |
| 6.15 | +2.1 | 13.6 | 73.1 | 89.2 | 24.1 | 464 |
| 6.15 | +2.8 | 13.1 | 80.7 | 91.9 | 23.9 | 439 |
| 6.15 | +3.5 | 12.6 | 83.3 | 91.4 | 23.2 | 431 |
| 6.30 | Field culture | 10.2 | 65.5 | 96.1 | 26.9 | 445 |
| 6.30 | +0.7 | 9.7 | 101.5 | 87.5 | 23.8 | 471 |
| 6.30 | +1.4 | 10.2 | 92.6 | 88.5 | 24.2 | 526 |
| 6.30 | +2.1 | 10.7 | 87.2 | 91.6 | 23.7 | 476 |
| 6.30 | +2.8 | 9.0 | 95.9 | 86.0 | 24.2 | 436 |
| 6.30 | +3.5 | 8.9 | 96.7 | 83.9 | 23.9 | 426 |

As shown in Table 2, in 2010, due to the insufficient duration of sunshine in the ripening stage compared to an average year, and a dramatic temperature decrease in the later part of the ripening stage, the amount of rice was the highest for rice transplantation on June 1$^{st}$, which was 520 kg/10a. However, as the day of rice transplantation was delayed, the amount of rice decreased.

For rice transplantation on June 1$^{st}$, which showed a comparably advanced heading stage, as temperature increased, the amount of rice drastically decreased and in the condition of a temperature increase of 3.5° C., the amount was very low, which was 217 kg/10a.

As the day of rice transplantation was delayed, a reduction in the amount of rice due to a temperature increase was comparably small, and the amount of rice was highest under the condition of a temperature increase of 1.4° C. For rice transplantation on June 1$^{st}$, the yield component which had the largest influence on the amount reduction in the temperature increase condition was ripening, and when temperature increased, a ripening ratio was drastically reduced.

EXAMPLE 6-4

Change in the Amount and Resveratrol Content Depending on the Day of Rice Transplantation The change in the resveratrol content depending on the day of rice transplantation of the resveratrol synthetic rice of the present invention was measured.

Figure 12:
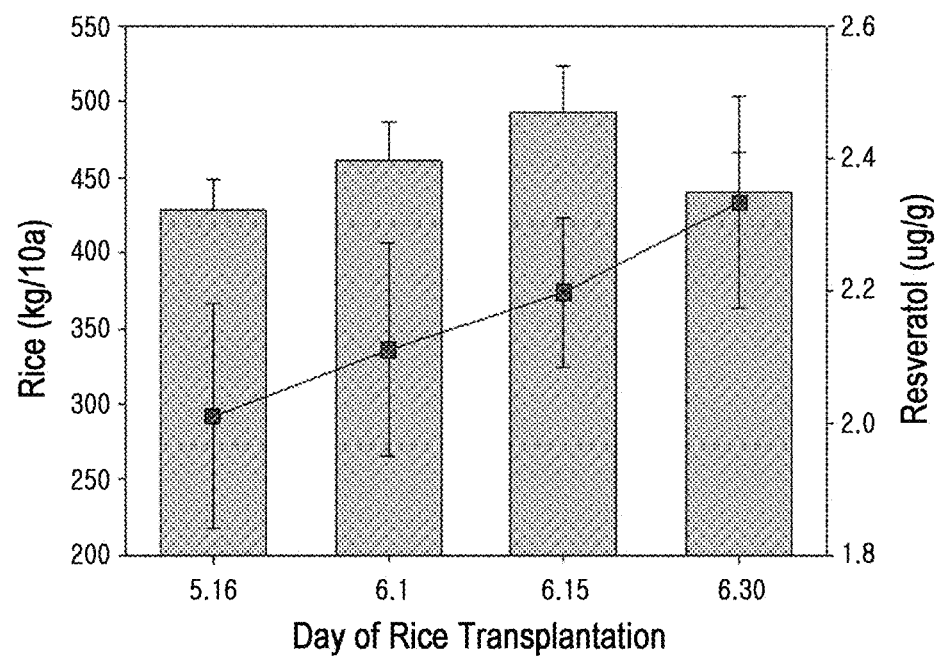
FIG. 12 is a schematic diagram illustrating the amount of rice and the content of resveratrol according to the day of rice transplantation of the transformed rice for biosynthesizing resveratrol of the present invention.

The resveratrol content increased as the day of rice transplantation was delayed, rice transplantation on June 15$^{th}$ showed the highest amount of rice and the highest resveratrol content (FIG. 12).

EXAMPLE 6-5

Changes in Resveratrol and Piceid Contents Depending on the Day of Rice Transplantation, Cultivating Temperature, and the Day of Harvest The changes in resveratrol and piceid contents depending on the day of rice transplantation, cultivating temperature, and the day of harvest of the resveratrol synthetic rice of the present invention were measured.

TABLE 3

The changes in the resveratrol content in seeds (milled rice) depending on the day of rice transplantation, cultivating temperature, and the day of harvest

| Day of rice trans- plan- tation | Temper- ature Treat- ment | 30 days after heading (μg/g) | | 40 days (μg/g) | | 50 days (μg/g) | |
|---|---|---|---|---|---|---|---|
| | | Piceid | Res- vera- trol | Piceid | Res- vera- trol | Piceid | Res- vera- trol |
| 6.1 | Field culture | 2.248 | 1.895 | 4.145 | 2.570 | 3.012 | 2.342 |
| 6.1 | 0.7 | 1.572 | 2.696 | 3.373 | 2.727 | 0.899 | 2.317 |
| 6.1 | 1.4 | 1.095 | 2.334 | 2.362 | 2.759 | 1.332 | 2.673 |
| 6.1 | 2.1 | 1.602 | 3.326 | 6.467 | 3.452 | 2.095 | 2.682 |
| 6.1 | 2.8 | 2.274 | 3.547 | 1.849 | 3.287 | 2.161 | 2.463 |
| 6.1 | 3.5 | 3.191 | 4.085 | 1.735 | 3.130 | 2.946 | 2.782 |
| 6.1 | Average | 1.997 | 2.981 | 3.322 | 2.988 | 2.074 | 2.543 |
| 6.15 | Field culture | 1.529 | 2.323 | 2.818 | 2.799 | 3.743 | 2.838 |
| 6.15 | 0.7 | 1.194 | 2.901 | 2.623 | 2.886 | 2.164 | 2.838 |
| 6.15 | 1.4 | 2.016 | 2.527 | 2.444 | 3.032 | 4.164 | 3.029 |
| 6.15 | 2.1 | 1.648 | 2.720 | 3.135 | 3.321 | 4.204 | 3.448 |
| 6.15 | 2.8 | 1.715 | 2.669 | 2.458 | 3.14 | 2.884 | 3.293 |
| 6.15 | 3.5 | 1.754 | 3.369 | 3.204 | 3.411 | 5.434 | 3.396 |
| 6.15 | Average | 1.643 | 2.752 | 2.780 | 3.098 | 3.766 | 3.140 |
| 6.30 | Field culture | 2.543 | 2.372 | 3.071 | 2.688 | 0.353 | 1.874 |
| 6.30 | 0.7 | 2.241 | 1.996 | 2.927 | 2.634 | 0.527 | 2.325 |
| 6.30 | 1.4 | 4.338 | 2.459 | 2.842 | 2.669 | 0.671 | 2.714 |
| 6.30 | 2.1 | 3.476 | 2.438 | 3.177 | 2.604 | 0.482 | 2.889 |
| 6.30 | 2.8 | 4.040 | 2.991 | 3.343 | 3.071 | 0.736 | 2.837 |
| 6.30 | 3.5 | 4.675 | 2.921 | 4.046 | 3.645 | 0.546 | 2.862 |
| 6.30 | Average | 3.552 | 2.530 | 3.234 | 2.885 | 0.553 | 2.584 |

TABLE 4

The changes in the piceid content in the plant body depending on the day of rice transplantation, cultivating temperature, and the day of harvest

| | | Piceid content (μg/g) | | |
|---|---|---|---|---|
| Day of rice transplantation | Temperature | 30 days after heading | 40 days | 50 days |
| 6.1 | Field culture | 8.8 | 3.6 | 4.6 |
| 6.1 | +0.7 | 6.7 | 3.7 | 5.7 |
| 6.1 | +1.4 | 8.5 | 5.1 | 7.1 |
| 6.1 | +2.1 | 9.1 | 9.0 | 7.2 |
| 6.1 | +2.8 | 8.0 | 6.8 | 8.1 |
| 6.1 | +3.5 | 10.4 | 4.0 | 7.9 |
| 6.1 | Average | 8.6 | 5.4 | 6.8 |
| 6.15 | Field culture | 8.5 | 3.7 | 8.4 |
| 6.15 | +0.7 | 6.2 | 3.7 | 1.7 |
| 6.15 | +1.4 | 5.6 | 5.3 | 4.0 |
| 6.15 | +2.1 | 7.6 | 9.3 | 5.0 |
| 6.15 | +2.8 | 3.2 | 7.0 | 4.8 |
| 6.15 | +3.5 | 10.1 | 4.0 | 2.9 |
| 6.15 | Average | 6.9 | 5.5 | 4.5 |
| 6.30 | Field culture | 8.3 | 4.8 | 8.4 |
| 6.30 | +0.7 | 6.1 | 3.2 | 1.7 |
| 6.30 | +1.4 | 5.3 | 3.7 | 3.9 |
| 6.30 | +2.1 | 7.1 | 4.3 | 4.8 |
| 6.30 | +2.8 | 4.5 | 5.4 | 4.8 |
| 6.30 | +3.5 | 9.6 | 7.9 | 3.0 |
| 6.30 | Average | 6.8 | 4.9 | 4.4 |

As shown in Table 3, as the day of rice transplantation was delayed, the resveratrol content was increased, and in the same rice transplantation conditions, the resveratrol content increased when treated with high temperature stress. The group, which was harvested 40 days after heading, had the overall high resveratrol content.

Further, as shown in Table 4, piceid is a glycoside form of resveratrol rice, and as ripening progressed the piceid content contained in leaves gradually decreased. However, when the day of rice transplantation is delayed, thereby causing delayed ripening or ripening to take place in high temperature conditions, the piceid content in leaves tended to be high. This was determined to be due to phytoalexin effects following high heat stress.

EXAMPLE 6-6

Changes in the Resveratrol Content in Seeds Depending on Harvest Conditions

The changes in the resveratrol content in seeds (brown rice) depending on harvest conditions of the resveratrol synthetic rice of the present invention were measured. As illustrated in FIG. 13, the resveratrol content in seeds increased under high heat conditions in the ripening stage, and in the conditions of a temperature increase of 2° C. or higher, the resveratrol content increased by 20% compared to the field culture conditions.

The increase in resveratrol under high temperature conditions for rice transplantations on June 1st and June 15th showed similar trends, but rice transplantation on June 30th was drastically increasing resveratrol as temperature increased.

EXAMPLE 6-7

Growth Characteristics Depending on the Difference Between Actual Regions

In order to investigate agricultural characteristics of the resveratrol synthetic rice of the present invention, agricultural characteristics of resveratrol synthase rice of the present invention and transformed Dongjin rice, which is a mother variety, as a comparative breed were examined.

Particularly, Dongjin, conventional transformed rice (transformed rice wherein two copies of a resveratrol synthase gene are inserted in a reverse direction in the 4$^{th}$ chromosome of natural rice), and resveratrol-enriched transgenic rice of the present invention were cultivated in the isolated field of planting spaces of 30 cm×15 cm with 3 seedlings per hill via 3 cycles of a randomized block design in 3 different regions, Iksan, Suwon, and Miryang. The growth characteristics and amount were examined.

TABLE 5

| Regional main growth characteristics and the yield component of rice | | | | | | | | | |
|---|---|---|---|---|---|---|---|---|---|
| Region | Systematic name | Heading stage (M.D) | Stem length (cm) | Panicle (#) | Number of grains per panicle (#) | Brown/rough rice ratio (%) | Ripening ratio (%) | Grain weight of brown rice (g) | Amount of rice (kg/10a) | Amount index number |
| Iksan | Dongjin | 8.20 | 89 | 12 | 104 | 82.7 | 93.3 | 23.9 | 521 | 100 |
| Iksan | conventional transformed rice | 8.25 | 81 | 12 | 99 | 82.2 | 92.3 | 22.0 | 496 | 95 |
| Iksan | transformed rice of the present invention | 8.24 | 87 | 11 | 111 | 82.3 | 90.0 | 24.6 | 519 | 100 |
| Suwon | Dongjin | 8.29 | 73 | 8 | 95 | 76.2 | 91.4 | 25.1 | 461 | 100 |
| Suwon | conventional transformed rice | 8.31 | 69 | 8 | 97 | 75.9 | 86.1 | 22.2 | 436 | 95 |
| Suwon | transformed rice of the present invention | 8.30 | 75 | 7 | 107 | 75.7 | 89.3 | 26.2 | 456 | 99 |
| Miryang | Dongjin | 8.15 | 85 | 13 | 108 | 82.1 | 92.6 | 22.1 | 542 | 100 |
| Miryang | conventional transformed rice | 8.22 | 77 | 13 | 103 | 82.0 | 88.5 | 20.0 | 519 | 96 |
| Miryang | transformed rice of the present invention | 8.23 | 84 | 11 | 112 | 81.5 | 88.3 | 22.4 | 539 | 99 |

As shown in Table 5, although Iksan and Miryang showed similar results in growth characteristics and amounts, all the experimental groups cultivated in Suwon showed delayed heading and a reduced height by 12 cm or more compared to those of Iksan. Due to reduced panicles, number of grains per panicle, and ripening ratio, the amount of rice was reduced by about 12% compared to those of Iksan. Compared to the comparative group, Dongjin rice, Iksan, Suwon, and Miryang all showed the same trend of the amount index number.

Further, after seeds cultivated in the isolated field were harvested and pounded by the above method, the resveratrol content in milled rice was analyzed.

TABLE 6

| Analysis on resveratrol and piceid contents | | |
|---|---|---|
| Systematic name | Resveratrol (μg/g) | Piceid (μg/g) |
| conventional transformed rice | 1.400.01 | 0.290.00 |
| transformed rice of the present invention | 2.010.06 | 0.420.03 |

As shown in Table 6, it was confirmed that 1.40 μg/g and 2.01 μg/g of resveratrol were synthesized in conventional transformed rice and the resveratrol-enriched transgenic rice of the present invention, respectively.

3-cycle samples of Dongjin, conventional transformed rice (transformed rice wherein two copies of a resveratrol synthase gene are inserted in a reverse direction into the $4^{th}$ chromosome of natural rice), and resveratrol synthetic rice of the present invention were cultivated in 3 different regions, Iksan, Suwon, and Miryang and were pounded and produced as milled rice, followed by analysis of the resveratrol content via HPLC.

TABLE 7

| Analysis of the resveratrol content in seeds (milled rice) cultivated in 3 regions | | | | |
|---|---|---|---|---|
| Region | Systematic name | Resveratrol (μg/g) | Piceid (μg/g) | Resveratrol content index number |
| Iksan | Dongjin | — | — | — |
| Iksan | conventional transformed rice | 1.400.01 | 0.290.00 | 100 |
| Iksan | transformed rice of the present invention | 2.010.06 | 0.420.03 | 100 |
| Suwon | Dongjin | — | — | — |
| Suwon | conventional transformed rice | 1.950.01 | 0.480.03 | 139 |
| Suwon | transformed rice of the present invention | 2.610.05 | 0.990.06 | 130 |
| Miryang | Dongjin | — | — | — |
| Miryang | conventional transformed rice | 1.750.01 | 0.390.05 | 125 |
| Miryang | transformed rice of the present invention | 2.270.06 | 0.590.06 | 129 |

As shown in Table 7, the resveratrol contents of both conventional transformed rice and resveratrol synthase rice of the present invention showed an increase by about 30% or more and 25% or more, respectively, in Suwon and Miryang, compared to Iksan. This is due to resveratrol synthesis increased depending on the difference in temperature of cultivating regions via phytoalexin effects of the resveratrol synthase gene.

EXAMPLE 7

Measuring Effects of Resveratrol-Enriched Rice in Animal Models Induced with a Metabolic Disease The effects of rice containing resveratrol of the present invention at high concentration on a metabolic disease were examined using animal models (mice) induced with a metabolic disease by a long-term high fat diet. Particularly, each of 15 C57BL/6 inbred mice was fed with a high fat diet for 12 weeks, thereby establishing models induced with a metabolic disease such as diabetes, obesity, hyperlipidemia, hypercholesterolemia, etc. Next, the feed produced from seeds of transformed rice or Dongjin rice was distributed to animals for 12 weeks. After 12 weeks of distribution, via blood sampling from a tail vein once every 3 weeks, blood glucose, cholesterol, etc., were analyzed, thereby examining the effects of resveratrol-enriched transgenic rice and transformed rice in animal models induced with a metabolic disease.

EXAMPLE 7-1

Comparative Measurement of Blood Glucose

As described above, after feeding feed for experimental animals, in which carbohydrate components were replaced with Dongjin rice and resveratrol-enriched transgenic rice to mice induced with a metabolic disease, the level of blood glucose was measured (FIG. 2).

As illustrated in FIG. 2, mice which consumed the feed produced from the transformed rice showed a decrease in blood glucose from the $8^{th}$ week, and the blood glucose dropped by 22.0% in the $12^{th}$ week. On the other hand, the control groups showed an equal or increased blood glucose level. Further, when fed with general feed including resveratrol (Resv) at an amount equivalent to that of feed produced from transformed rice, mice did not show a remarkable difference, thereby confirming that the effect of transformed rice on reducing blood glucose is superior to that of simply containing resveratrol.

EXAMPLE 7-2

Comparative Measurement of Blood Lipid Metabolism

As described above, after feeding the feed in which carbohydrate components were replaced with Dongjin rice and resveratrol-enriched transgenic rice to mice induced with a metabolic disease, the total cholesterol in blood, the total natural fat in blood, and LDL and HDL cholesterol in blood were measured (FIG. 3).

As illustrated in FIG. 3, mice which consumed feed produced from transformed rice showed a reduction of the total cholesterol in blood by 27.0%, the total natural fat in blood by 37.4%, and LDL cholesterol in blood by 59.6%, while showing an increase of HDL cholesterol in blood by 14.8%, which acts to prevent a metabolic disease.

Other control groups showed no effects or effects lowered than the group which consumed feed produced from transformed rice. Further, even when compared to the group fed with general feed including resveratrol (Resv) at an amount equivalent to that of the feed produced from the transformed unhulled rice, the group which consumed the feed produced from the transformed rice exhibited effects of improving blood lipids. This confirmed that the effect of transformed rice on improving blood lipids is superior to that of simply containing resveratrol.

EXAMPLE 7-3

Comparative Measurement of Weight and Body Fat

Figure 4A:
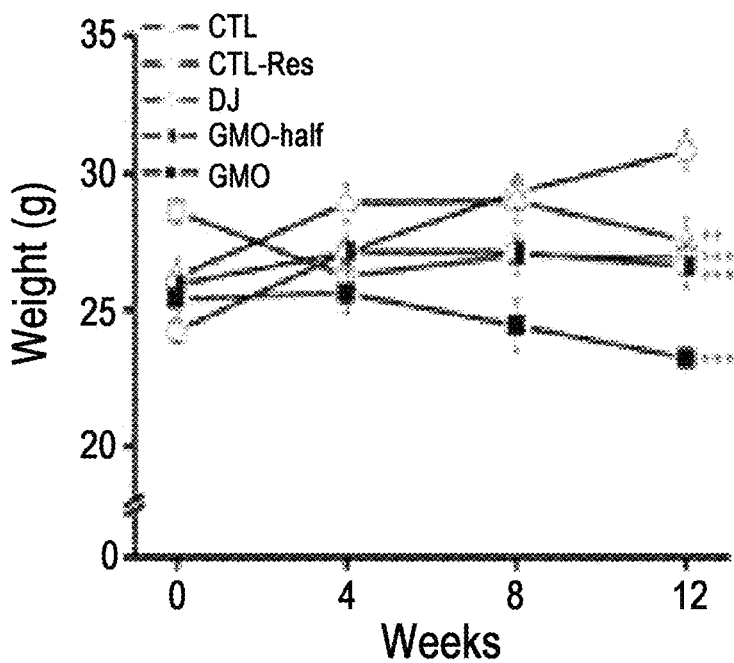
Figure 4B:
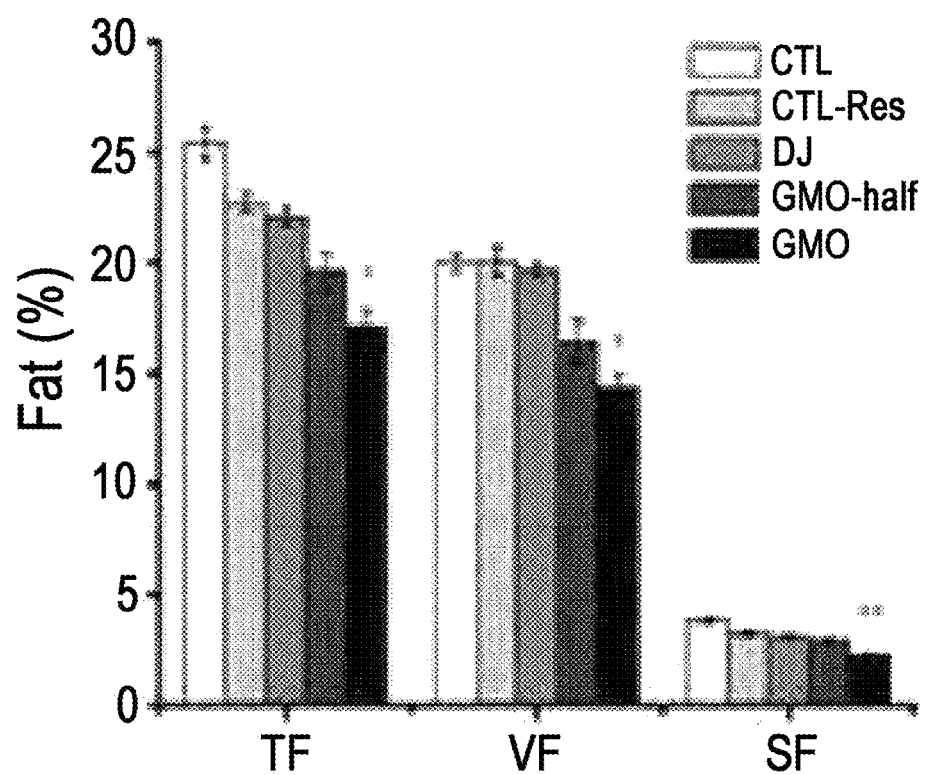
Figure 4C:
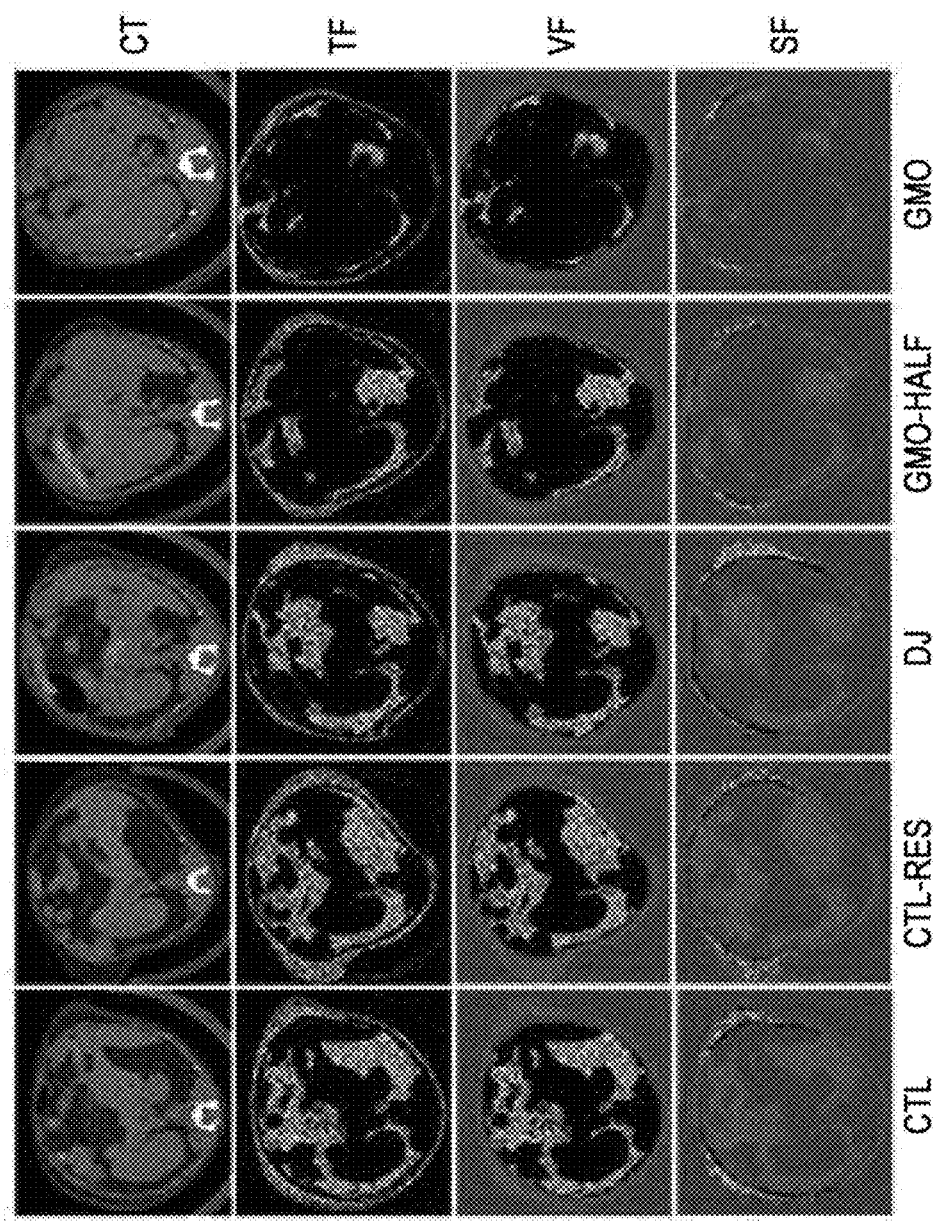

As described above, after feeding the feed in which carbohydrate components are replaced with Dongjin rice and resveratrol-enriched transgenic rice to mice induced with a metabolic disease, the weight change and the total fat were measured (FIG. 4).

As illustrated in FIG. 4, mice which consumed the feed produced from transformed rice showed the weight reduced by 24.7%. Also, when the total fat was measured using in vivo micro CT, the total fat was reduced by 21.55% (control group by 25.43%), visceral fat was reduced by 16.33% (control group by 20.02%), and subcutaneous fat was reduced by 3.1% (control group by 3.83%). Thus, it was confirmed that the amount of the total fat was significantly reduced compared to the control group.

COMPARATIVE EXAMPLE 1

Effects of Resveratrol Synthetic Rice

In order to compare the effects to transformed rice, in which the same resveratrol synthase gene was inserted in a different chromosome, the effects of the transformed rice, in which the same resveratrol synthase gene was inserted into the $4^{th}$ chromosome of natural rice, were examined.

First, transformed rice, in which the same resveratrol synthase gene was inserted into the $4^{th}$ chromosome of natural rice, was produced by the methods described in Examples 1 to 3. Further, it was confirmed that the resveratrol synthase gene was inserted at the $29,358,342^{nd}$ base of the $4^{th}$ chromosome by the method described in Example 4, and was named as the control transformed rice.

It was confirmed that the control transformed rice contains 1.60±0.05 μg/g (brown rice) or 1.41±0.014 μg/g (milled rice) of resveratrol, and 3.21±0.06 μg/g (brown rice) or 0.48±0.03 μg/g (milled rice) of piceid, thereby confirming it as resveratrol synthetic rice in which the resveratrol synthase gene is normally functioning.

The effects of another resveratrol synthetic rice produced as such were confirmed by the same method as Example 7 in animal models with an induced metabolic disease.

COMPARATIVE EXAMPLE 1-1

Comparative Measurement of Blood Glucose

Figure 5:
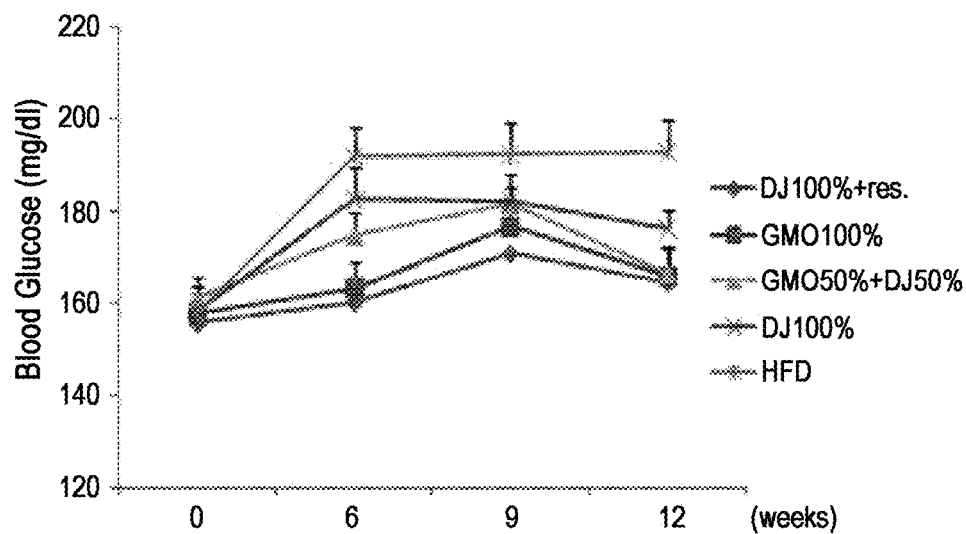
Figure 6:
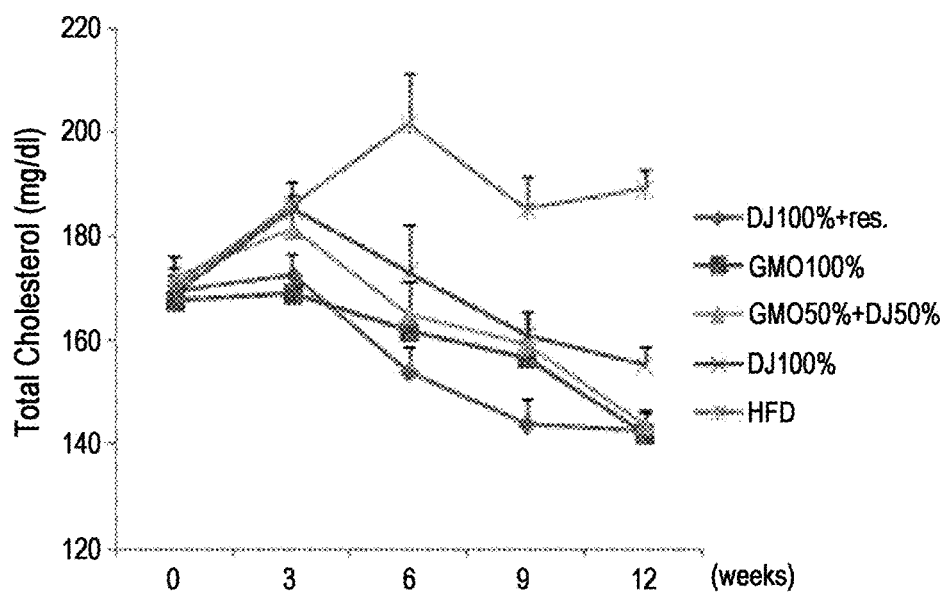
Figure 7:
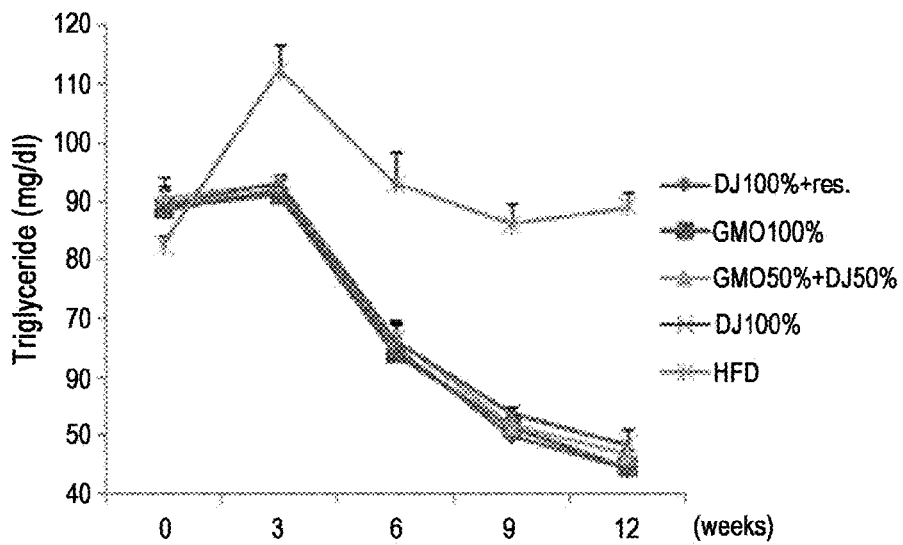
Figure 8:
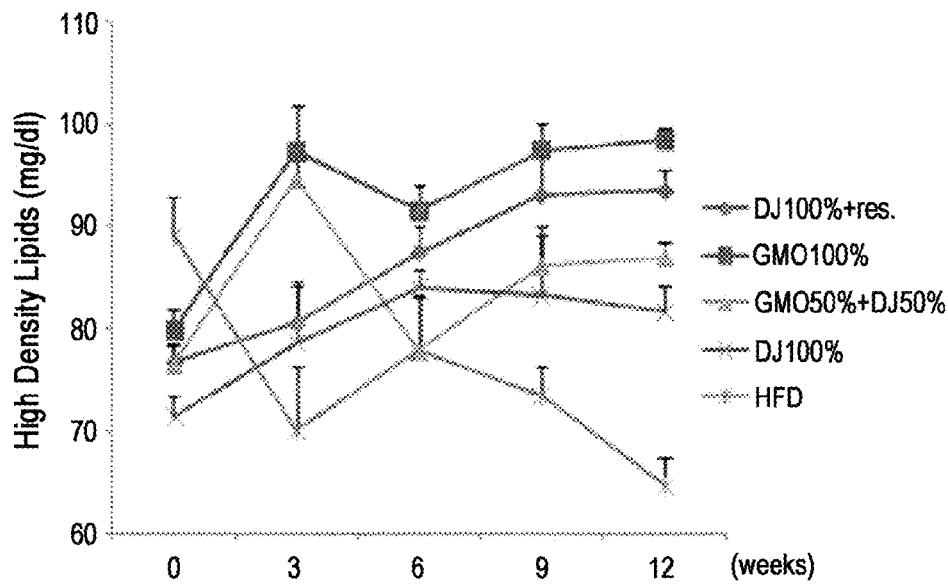
Figure 9:
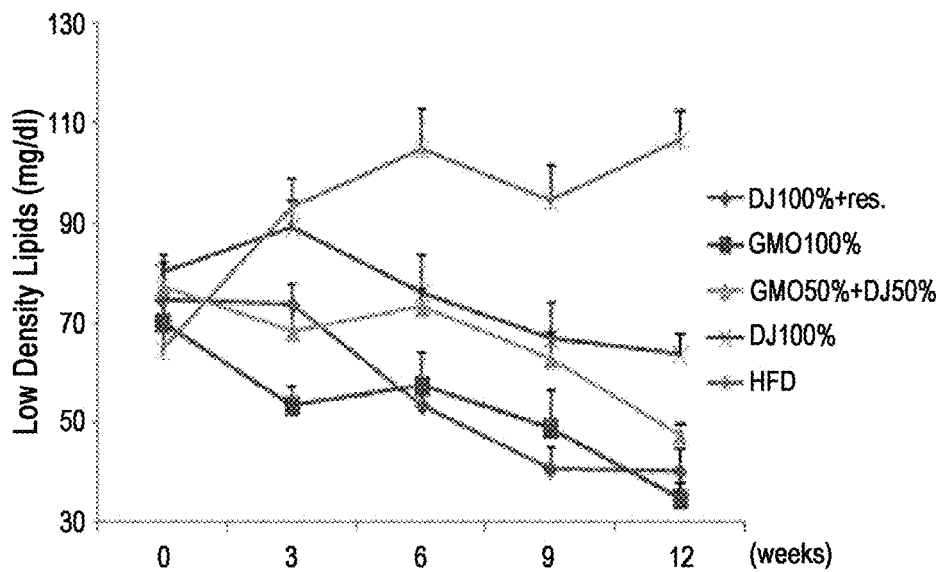

As described above, after feeding the feed, in which carbohydrate components were replaced with Dongjin rice and resveratrol-enriched transgenic rice, to mice with an induced metabolic disease, the level of blood glucose was measured (FIG. 5).

As illustrated in FIG. 5, the mice which consumed the control transformed rice showed a higher blood glucose level compared to the group which consumed Dongjin rice containing the equivalent amount of resveratrol, over the entire experimental period.

Thus, FIG. 2, which illustrates the experiment about transformed rice, shows that the effect of reducing blood glucose level was superior when the transformed rice was consumed, compared to when the feed containing an equivalent amount of resveratrol was consumed. However, FIG. 5 which illustrates the experiment about the control transformed rice shows that the control transformed rice exhibits an equivalent or inferior effect to that of the feed containing an equivalent amount of resveratrol.

COMPARATIVE EXAMPLE 1-2

Comparative Measurement of Blood Lipid Metabolism

As described above, after feeding the feed, in which carbohydrate components were replaced with Dongjin rice and resveratrol-containing transformed rice, to mice induced with a metabolic disease, the total cholesterol in blood, the amount of the total natural fat in blood, and LDL and HDL cholesterol in blood were measured (FIGS. 6 to 9).

As illustrated in FIGS. 6 to 9, mice which consumed the control transformed rice showed no difference or inferior effects in the total cholesterol in blood, the total natural fat in blood, and LDL cholesterol in blood, compared to the group which consumed Dongjin rice. However, although HDL cholesterol in blood was somewhat increased, the difference was not significant.

Thus, FIG. 3, which illustrates the experiment about transformed rice, shows that the effects of reducing the total cholesterol in blood, the total natural fat in blood, and LDL cholesterol in blood and increasing HDL cholesterol in blood were observed when the transformed rice was consumed, compared to when feed containing an equivalent amount of resveratrol was consumed. However, FIGS. 6 to 9, which illustrate the experiment about the control transformed rice, show that the control transformed rice exhibited inferior effects to those of the feed containing an equivalent amount of resveratrol.

COMPARATIVE EXAMPLE 1-3

Comparative Measurement of Weight

Figure 10:
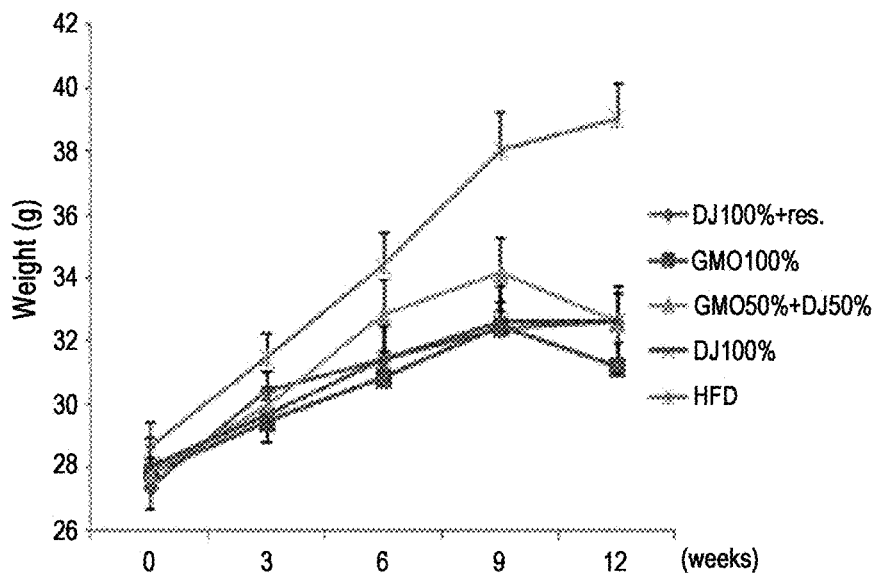
FIG. 10 is a schematic diagram illustrating the effects of the transformed rice for biosynthesizing resveratrol of the present invention and the control transformed rice on weight changes in animal models induced with a metabolic disease. In the drawing, CTL refers to the control group, DJ to Dongjin rice, res to resveratrol, GMO to the control transformed rice, and HFD to high fat feed.

As described above, after feeding the feed in which carbohydrate components were replaced with Dongjin rice and resveratrol-containing transformed rice to mice with an induced metabolic disease, the weight change was measured (FIG. 10).

As illustrated in FIG. 10, mice which consumed the control transformed rice showed no difference up to 9 weeks and reduced weight from 12 weeks, compared to the group which consumed Dongjin rice containing the equivalent amount of resveratrol.

However, compared to the difference of 24.7% in the experiment about the transformed rice in FIG. 4a, the effects of reducing weight of the control transformed rice was as weak as about 6%.

In summary of the results, the present invention in which a resveratrol synthase gene is inserted into the $12^{th}$ chromosome of natural rice exhibits superior effects of preventing or treating a metabolic disease compared to transformed rice, in which the same gene is inserted into a different chromosome.

Based on the above description, it should be understood by one of ordinary skill in the art that other specific embodiments may be employed in practicing the invention without departing from the technical idea or essential features of the present invention. In this regard, the above-described examples are for illustrative purposes only, and the invention is not intended to be limited by these examples. The scope of the present invention should be understood to include all of the modifications or modified forms derived from the meaning and scope of the following claims or its equivalent concepts, rather than the above detailed description.

Deposit Designation

BUDAPEST TREATY ON THE INTERNATIONAL RECOGNITION OF THE DEPOSIT
OF MICROORGANISMS FOR THE PURPOSE OF PATENT PROCEDURE

INTERNATIONAL FORM

RECEIPT IN THE CASE OF AN ORIGINAL DEPOSIT issued pursuant to Rule 7.1

TO : Baek, So-Hyeon
National Institute of Crop Science Rural Development Administration
457 Pyeongdong-ro, Iksan-si, Jeollabuk-do 570-080
Republic of Korea

| I. IDENTIFICATION OF THE MICROORGANISM ||
|---|---|
| Identification reference given by the DEPOSITOR: | Accession number given by the INTERNATIONAL DEPOSITARY AUTHORITY: |
| Resveratrol-enriched rice | KCTC 12529BP |

| II. SCIENTIFIC DESCRIPTION AND/OR PROPOSED TAXONOMIC DESIGNATION |
|---|
| The microorganism identified under I above was accompanied by:<br>[ x ] a scientific description<br>[ ] a proposed taxonomic designation<br>(Mark with a cross where applicable) |

| III. RECEIPT AND ACCEPTANCE |
|---|
| This International Depositary Authority accepts the microorganism identified under I above, which was received by it on December 05, 2013. |

| IV. RECEIPT OF REQUEST FOR CONVERSION |
|---|
| The microorganism identified under I above was received by this International Depositary Authority on      and a request to convert the original deposit to a deposit under the Budapest Treaty was received by it on |

| V. INTERNATIONAL DEPOSITARY AUTHORITY ||
|---|---|
| Name: Korean Collection for Type Cultures<br><br>Address: Korea Research Institute of Bioscience and Biotechnology (KRIBB)<br>125 Gwahak-ro, Yuseong-gu,<br>Daejeon 305-806<br>Republic of Korea | Signature(s) of person(s) having the power to represent the International Depositary Authority of authorized official(s):<br><br>BAE, Kyung Sook, Director<br>Date: December 09 2013 |

Form BP/4 (KCTC Form 17)                      sole page

What is claimed is:

1. Resveratrol-enriched transgenic rice for biosynthesizing resveratrol, wherein two copies of a resveratrol synthase gene are expressibly inserted in an opposing direction from each other at the same location after the 572nd base in the region of a nucleotide sequence represented by SEQ ID NO: 7 in the 12th chromosome of natural unhulled rice.

2. The rice according to claim 1, wherein the resveratrol synthase gene originates from *Arachis hypogaea*.

3. The rice according to claim 1, wherein the resveratrol synthase gene consists of a nucleotide sequence represented by SEQ ID NO: 1.

4. The rice according to claim 1, wherein the rice is rice deposited under Accession No. KCTC12529BP.

5. The rice according to claim 1, wherein the rice comprises about 2 μg/g to 5.3 μg/g of resveratrol in the case of brown rice and about 1.8 μg/g to 4.1 μg/g of resveratrol in the case of milled rice when matured.

6. The rice according to claim 1, further biosynthesizing piceid.

7. The rice according to claim 6, wherein the rice comprises about 1.0 μg/g to 6.5 μg/g of piceid in the case of milled rice upon maturation.

8. Seed of rice produced from the rice according to any one of claims 1 to 3 and 4 to 7.

9. A health functional food composition for preventing and improving a metabolic disease, comprising seed of rice produced from the resveratrol-enriched transgenic rice for biosynthesizing resveratrol, wherein two copies of a resveratrol synthase gene are expressibly inserted in an opposing direction from each other at the same location after the 572nd base in the region of a nucleotide sequence represented by SEQ ID NO: 7 in the 12th chromosome of natural unhulled rice.

10. The health functional food composition according to claim 9, wherein the natural rice is natural Dongjin rice.

11. The health functional food composition according to claim 9, wherein the resveratrol-enriched transgenic rice for biosynthesizing resveratrol, further biosynthesizes piceid.

12. The health functional food composition according to claim 9, wherein the metabolic disease is selected from the group consisting of obesity, diabetes, hyperlipidemia, and hypercholesterolemia.

13. An animal feed composition for preventing and improving a metabolic disease, comprising seed of rice produced from the resveratrol-enriched transgenic rice for biosynthesizing resveratrol, wherein two copies of a resveratrol synthase gene are expressibly inserted in an opposing direction from each other at the same location after the $572^{nd}$ base in the region of a nucleotide sequence represented by SEQ ID NO: 7 in the $12^{th}$ chromosome of natural unhulled rice.

14. A pharmaceutical composition for preventing and improving a metabolic disease, comprising seed of rice produced from the resveratrol-enriched transgenic rice for biosynthesizing resveratrol, wherein two copies of a resveratrol synthase gene are consecutively and expressibly inserted in an opposing direction from each other at the same location after the $572^{nd}$ base in the region of a nucleotide sequence represented by SEQ ID NO: 7 in the $12^{th}$ chromosome of natural unhulled rice.

\* \* \* \* \*

SEQUENCE LISTING

<160> NUMBER OF SEQ ID NOS: 12

<210> SEQ ID NO 1
<211> LENGTH: 1170
<212> TYPE: DNA
<213> ORGANISM: Arachis hypogaea

<400> SEQUENCE: 1

| | | |
|---|---|---|
| atggtgtctg tgagtggaat tcgcaaggtt caaagggcag aaggtccagc aactgtattg | 60 |
| gcaattggaa cagcaaatcc accgaactgt attgatcaga gtacatatgc agattattat | 120 |
| tttagagtaa ccaatagcga acacatgact gatctcaaga gaaatttca gcgcatctgt | 180 |
| gagagaacac agatcaagaa cagacatatg tacttaacag aagagatact aaaagaaaat | 240 |
| cctaacatgt gtgcatacaa ggcaccgtca ttggatgcaa gagaagacat gatgatcagg | 300 |
| gaggtaccaa gagttggaaa agaggctgca accaaggcca tcaaggaatg gggccagcca | 360 |
| atgtctaaga tcacacattt gatcttctgc accaccagcg gcgttgcgtt gcctggcgtt | 420 |
| gattacgaac tcatcgtact tttagggctg gacccatgcg tcaagaggta catgatgtac | 480 |
| caccaaggtt gcttcgctgg tggcactgtc cttcgtttgg ctaaggactt ggctgaaaac | 540 |
| aacaaggatg ctcgtgtact tatcgtttgt tctgagaata ccgcagtcac tttccgcggt | 600 |
| cctagtgaga cagacatgga tagtcttgta ggacaagcat tgtttgccga tggagctgct | 660 |
| gcgattatca ttggttctga tcctgtgcca gaggttgaga agcctatctt tgagcttgtt | 720 |
| tcgaccgatc aaaaacttgt ccctggcagc catggagcca tcgtggtctc cttcgtgaa | 780 |
| gttggactta cattctatct taacaagagt gttcctgata ttatttcgca aaatatcaat | 840 |
| gacgcgctca ataaagcttt tgatccattg ggtatttctg attataactc aatattttgg | 900 |
| attgcacatc ctggtgggcg tgcaattttg gaccaggttg aacagaaggt gaacttgaag | 960 |
| ccagagaaga tgaaagccac tagagatgtg cttagcaatt atggtaacat gtcaagtgcc | 1020 |
| tgtgtgttct tcattatgga tttgatgagg aagaggtctc ttgaagaagg acttaaaact | 1080 |
| accggagaag gacttgattg gggtgtgctt tttggctttg gtcctggtct cactattgaa | 1140 |
| actgtcgttc tccgcagtgt ggccatataa | 1170 |

<210> SEQ ID NO 2
<211> LENGTH: 22
<212> TYPE: DNA
<213> ORGANISM: Artificial Sequence
<220> FEATURE:
<223> OTHER INFORMATION: Synthetic Primer

<400> SEQUENCE: 2
atggtgtctg tgagtggaat tc    22

<210> SEQ ID NO 3
<211> LENGTH: 19
<212> TYPE: DNA
<213> ORGANISM: Artificial Sequence
<220> FEATURE:
<223> OTHER INFORMATION: Synthetic Primer

<400> SEQUENCE: 3
cgttatatgg ccacactgc    19

<210> SEQ ID NO 4
<211> LENGTH: 23
<212> TYPE: DNA
<213> ORGANISM: Artificial Sequence

```
<220> FEATURE:
<223> OTHER INFORMATION: Synthetic Primer

<400> SEQUENCE: 4
cggatccatg gtgtctgtga gtg                                                  23

<210> SEQ ID NO 5
<211> LENGTH: 22
<212> TYPE: DNA
<213> ORGANISM: Artificial Sequence
<220> FEATURE:
<223> OTHER INFORMATION: Synthetic Primer

<400> SEQUENCE: 5
cgagctccgt tatatggcca ca                                                   22

<210> SEQ ID NO 6
<211> LENGTH: 389
<212> TYPE: PRT
<213> ORGANISM: Arachis hypogaea

<400> SEQUENCE: 6
```

Met Val Ser Val Ser Gly Ile Arg Lys Val Gln Arg Ala Glu Gly Pro
1               5                   10                  15

Ala Thr Val Leu Ala Ile Gly Thr Ala Asn Pro Pro Asn Cys Ile Asp
            20                  25                  30

Gln Ser Thr Tyr Ala Asp Tyr Tyr Phe Arg Val Thr Asn Ser Glu His
        35                  40                  45

Met Thr Asp Leu Lys Lys Lys Phe Gln Arg Ile Cys Glu Arg Thr Gln
    50                  55                  60

Ile Lys Asn Arg His Met Tyr Leu Thr Glu Glu Ile Leu Lys Glu Asn
65                  70                  75                  80

Pro Asn Met Cys Ala Tyr Glu Ala Pro Ser Leu Asp Ala Arg Glu Asp
                85                  90                  95

Met Met Ile Arg Glu Val Pro Arg Val Gly Lys Glu Ala Ala Thr Lys
            100                 105                 110

Ala Ile Lys Glu Trp Gly Gln Pro Met Ser Lys Ile Thr His Leu Ile
        115                 120                 125

Phe Cys Thr Ala Ser Gly Val Ala Leu Pro Gly Val Asp Tyr Glu Leu
    130                 135                 140

Ile Val Leu Leu Gly Leu Asp Pro Cys Val Lys Arg Tyr Met Met Tyr
145                 150                 155                 160

His Gln Gly Cys Phe Ala Gly Gly Thr Val Leu Arg Leu Ala Lys Asp
                165                 170                 175

Leu Ala Glu Asn Asn Lys Asp Ala Arg Val Leu Ile Val Cys Ser Glu
            180                 185                 190

Asn Thr Ala Ile Thr Phe Arg Gly Pro Ser Glu Thr Asp Met Asp Ser
        195                 200                 205

Leu Val Gly Gln Ala Leu Phe Ala Asp Gly Ala Ala Ile Ile Ile
    210                 215                 220

Gly Ser Asp Pro Val Pro Glu Val Glu Lys Pro Ile Phe Glu Ile Val
225                 230                 235                 240

Ser Thr Asp Gln Lys Leu Val Pro Gly Ser His Gly Ala Ile Gly Gly
                245                 250                 255

Leu Leu Arg Glu Val Gly Leu Thr Phe Tyr Leu Asn Lys Ser Val Pro
            260                 265                 270

Asp Ile Ile Ser Gln Asn Ile Asn Asp Ala Leu Ser Lys Ala Phe Asp

```
                275                 280                 285
Pro Leu Gly Ile Phe Asp Tyr Asn Ser Ile Phe Trp Ile Ala His Pro
        290                 295                 300

Gly Gly Arg Ala Ile Leu Asp Gln Val Glu Gln Lys Val Asn Leu Lys
305                 310                 315                 320

Pro Glu Lys Met Lys Ala Thr Arg Asp Val Leu Ser Asn Tyr Gly Asn
                325                 330                 335

Met Ser Ser Ala Cys Val Phe Phe Ile Met Asp Leu Met Arg Lys Lys
            340                 345                 350

Ser Leu Lys Glu Gly Leu Lys Thr Thr Gly Glu Gly Leu Asp Trp Gly
        355                 360                 365

Val Leu Phe Gly Phe Gly Pro Gly Leu Thr Ile Glu Thr Val Val Leu
    370                 375                 380

Arg Ser Val Ala Ile
385

<210> SEQ ID NO 7
<211> LENGTH: 1101
<212> TYPE: DNA
<213> ORGANISM: Oryza sativa

<400> SEQUENCE: 7
gcctcgtcta cgaggccaac gcccgtatga gggaccccgt ctacggctgc gtcgccgcca      60
tctccttcct ccagaaccaa gtctcccagc tccagatgca gctcgccctc gcccacgccg     120
agaccgccgc cctgcaactc cagctgcagc agcagcacca agatcaagat gaccaccacc     180
accagcagtg catcctggag aatgctgctg ctcatcacca gctgatgctg caggaggcat     240
tcctcaagaa agagtccatg tggacataat tgtagtagat gctttctagt aaatcttat      300 gcttcgattg atatgatttg atgttgcaca agatttata gtaaatcttt gtgcttgttg      360
tcttctctta cgtaatttcc ggaaagaatg aaaatgaaga caacaattc ggtctcatta      420 gcctacctca tatccccatt tctgttcaaa tgctgtatta gcaagacaga aactgattgg     480
ctttctgaaa cacctgttgg cttcatgaac catcaattca gctcccatgc atgcacaagt     540
ttcagacaag ccttttgctt tcggagatat ggttgtttgc ttggtaaggg tcagtgatgt     600
gggacacatt aatttgtctt cacatggtct ctagttctag tacagtagga tccagatagt     660
atgtacacga actaattaag cacctcaaac caccccaaac tcaattaagt agcaggagag     720
ctaatgatat tagaagtcct gatctcacct actagattcc taagttctct acacgggaca     780
tgtgtccttt ctgtgctagg tctatatcat acctggactt cactaatact ccaaatccaa     840
tatcatacct ggagtactaa tttgtcaaat ccaatgttgt aaaataccta cgcatcagaa     900
tatgagttgg ttgatcgatc ctacaaaaca agagttgagt gcccgtgtca tcaaagggac     960
caacacagac aaaccaaagg ttgtctcttt cttgagaaag gaataatttc cagctatgct    1020
taatttggtt gttttttta gtaatgatat attaagatgg agtccttta acagcttgtt     1080 tttataaact tgatcatgat t                                             1101

<210> SEQ ID NO 8
<211> LENGTH: 38
<212> TYPE: DNA
<213> ORGANISM: Artificial Sequence
<220> FEATURE:
<223> OTHER INFORMATION: 1st T-DNA Insertion Initiation Region

<400> SEQUENCE: 8
```

-continued

```
ttgtggtgta aacaaattga cgcttagaca acttaata                          38

<210> SEQ ID NO 9
<211> LENGTH: 35
<212> TYPE: DNA
<213> ORGANISM: Artificial Sequence
<220> FEATURE:
<223> OTHER INFORMATION: End of 1st T-DNA

<400> SEQUENCE: 9
ggcgaatgcc ttcagtttaa actatcagtg tttga                             35

<210> SEQ ID NO 10
<211> LENGTH: 69
<212> TYPE: DNA
<213> ORGANISM: Artificial Sequence
<220> FEATURE:
<223> OTHER INFORMATION: Start of 2nd T-DNA

<400> SEQUENCE: 10
actgttggga agggcgatcg atcggtgcgg gccttcttgc tattacgcca gctggcgaaa   60
gggggatgt                                                          69

<210> SEQ ID NO 11
<211> LENGTH: 38
<212> TYPE: DNA
<213> ORGANISM: Artificial Sequence
<220> FEATURE:
<223> OTHER INFORMATION: 2nd T-DNA Insertion Termination Region

<400> SEQUENCE: 11
tattaagttg tctaagcgtc aatttgttta caccacaa                          38

<210> SEQ ID NO 12
<211> LENGTH: 80
<212> TYPE: DNA
<213> ORGANISM: Oryza sativa

<400> SEQUENCE: 12 cctttttgctt tcggagatat ggttgtttgc ttggtaaggg tcagtgatgt gggacacatt  60
aatttgtctt cacatggtct                                              80
```